US 6,306,626 B1

(12) United States Patent
Rosenblum et al.

(10) Patent No.: US 6,306,626 B1
(45) Date of Patent: Oct. 23, 2001

(54) ANTI-IGM MONOCLONAL ANTIBODIES AND METHODS OF THEIR USE

(75) Inventors: Michael G. Rosenblum, Sugar Land; Nicholas J. Donato, Houston, both of TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 08/192,507

(22) Filed: Feb. 7, 1994

Related U.S. Application Data

(63) Continuation-in-part of application No. 08/139,613, filed on Oct. 20, 1993, now abandoned, which is a continuation of application No. 07/832,663, filed on Feb. 4, 1992, now abandoned, which is a continuation of application No. 07/515,974, filed on Apr. 27, 1990, now abandoned.

(51) Int. Cl.$^7$ ........................ A61K 39/395; C07K 16/42; C12N 15/06; C12N 15/08
(52) U.S. Cl. ........................ 435/70.21; 424/178.1; 424/183.1; 530/391.1; 530/391.3; 530/391.7; 435/449
(58) Field of Search .................. 530/388.2, 388.73, 530/391.7; 435/240.27, 172.3, 70.21; 424/178.1, 183.1

(56) References Cited

PUBLICATIONS

Julius, Eur. J. Immunol, 14:753–7 1984.*
Kung et al., J. Immunol. 127:873–6 1981.*
Lambert et al. J. Biol. Chem. 260:12035–41, 1985.*
Taylor et al., Nature New Biology 233:225–9, 1971.*
Uletta et al. Science 238: 1098–1104, 1987.*
DeClercq et al. Mtds Inenzymology 121: 234–238, 1986.*
Brady et al., J Radation Oncol., Biol., Phys 13: 1535–44, 1987.*

* cited by examiner

*Primary Examiner*—Anthony C Caputa
*Assistant Examiner*—Karen A. Canella
(74) *Attorney, Agent, or Firm*—Benjamin Aaron Adler

(57) ABSTRACT

The present invention provides an anti-IgM antibody conjugate comprising: a monoclonal antibody which binds selectively to IgM antibody, does not bind to $IgG_1$ or $IgG_2$ antibody, and has a G isotype; and a cytotoxic moiety conjugated to said monoclonal antibody. The present invention also provides a method for collecting hybridoma producing IgG isotype monoclonal antibodies comprising: treating a hybrid cell population with a monoclonal antibody which has a G isotype and binds selectively to IgM antibody but does not bind to $IgG_1$ or $IgG_2$ antibody; subjecting said resulting immuncomplexed cells to sorting; and collecting the cells which have not complexed with said antibodies.

12 Claims, 25 Drawing Sheets

ANTI-IGM MONOCLONAL ANTIBODIES AND METHODS OF THEIR USE

CROSS-REFERENCE TO RELATED APPLICATION

This application is a continuation-in-part of U.S. patent application Ser. No. 08/139,613, filed Oct. 20, 1993, now abandoned which is a continuation of U.S. patent application Ser. No. 07/832,663, filed Feb. 4, 1992, now abandoned, which is a continuation of U.S. patent application Ser. No. 07/515,974, filed Apr. 27, 1990, now abandoned.

BACKGROUND OF THE INVENTION

1. Field of the Invention

The present invention relates generally to the fields of immunology and monoclonal antibody production. More particularly, the present invention concerns anti-IgM monoclonal antibodies and methods for their use.

2. Description of the Related Art

Since the initial description of monoclonal antibodies, the development of technology to produce immortalized lymphocytes capable of producing antibodies of predetermined specificity has had a major impact on both clinical and basic scientific research as well as the therapeutic modalities available for the diagnosis and treatment of a wide variety of pathological conditions.

Antibodies are endogenous proteins produced by the immune system in response to antigenic stimuli. These proteins specifically bind to antigen molecules at defined sites (epitopes). Polyclonal antibodies are derived from immunization of animals with antigens and bind to these antigens at multiple epitopes. Monoclonal antibodies, on the other hand, are a specific, defined set of antibodies which are derived from a single clone (monoclone) of cells producing a specific antibody. In contrast to polyclonal antibodies monoclonal antibodies bind to only one specific epitope on the antigen molecule.

Although the technology for the generation of monoclonal antibodies has existed for some time, the current methodology is time-consuming, laborious and often results in the production of antibodies which, although specific for the target antigen, are of relatively low affinity for the antigen, and thus are of limited usefulness in a wide variety of applications.

Among the difficulties encountered in the production of useful and clinically relevant monoclonal antibodies is the abundance of antibodies of the IgM sub-type obtained from hybridomas produced by standard in vivo or in vitro immunization procedures. The IgM sub-type antibodies are generally of low affinity, are difficult to purify and often comprise the bulk of antibodies produced by hybridomas. In addition, in mixed cultures of IgM and IgG secreting hybridoma cells, IgM secreting cells often overgrow the IgG secreting hybrid cells.

Part of the laborious procedure for the production of hybridomas is the elimination of the IgM producing hybridoma cells produced after a cell fusion. This is generally done by cloning the cells by limiting dilution, growing up the individual cells into colonies, and testing each colony individually to determine which colonies produce IgG sub-type antibodies. Generally, the IgG producing hybridoma cells are then further analyzed to determine the antigen specificity of the antibodies produced.

Although antibodies have been reported which are directed against epitopes on the IgM antibody, all tested to date were also reactive with IgG sub-type antibodies.

Linking cytotoxic agents to antibodies to make "immunotoxins" has been disclosed by the applicants and others. Recent interest has centered on immunotoxins of monoclonal antibodies conjugated to the enzymatically active portions (A chains) of toxins of bacterial or plant origin via hetero-bifunctional agents. Nevelle, D. M. and Youle, R. J., *Immunol Rev* (1982) 62: 75–91; Ross, W. C. J., et al., *European J Biochem* (1980) 104; Vitteta, E. S., et al., *Immunol Rev* (1982) 62: 158–183; Raso, V., et al., *Cancer Res* (1982) 42: 457–464; Trowbridge, I. W. and Domingo, D. L., *Nature (Lond)* (1981) 294: 171–173.

SUMMARY OF THE INVENTION

A principal aspect of the invention concerns rat monoclonal antibodies that: (a) bind selectively to IgM sub-type antibodies; (b) are IgGs; and (c) do not bind to $IgG_1$ or $IgG_2$ sub-type. The preferred embodiment of these antibodies is one designated 2G10, and functional equivalents thereof.

The rat x rat hybridomas that produce the above described antibodies and progeny of those hybridomas are other aspects of the invention.

The invention also includes a method of preparing a hybridoma as defined above comprising fusing rat tumor cells with rat splenocytes obtained from a rat immunized with murine IgM sub-type immunogen and selecting for hybridomas producing antibody as defined above.

A further aspect of the invention is a method of producing antibody as defined above comprising culturing a hybridoma having the ability to produce such antibody, or optionally a hybridoma which has been prepared by effecting a method as described above.

Another aspect of the invention relates to immunotoxins and their preparation by conjugating (a) the above described monoclonal antibodies, and (b) a cytotoxic moiety or magnetic beads.

Another aspect of the invention concerns labeled derivatives of the above described monoclonal antibodies that are labeled with a detectable label that permits the derivatives to be used in targeting, specific selection or sorting.

Another aspect of the invention concerns a method of killing IgM producing hybridoma or B cells by contacting the cells with a cytocidally effective amount of one or more of the above described immunotoxins.

Other aspects of the invention are direct and indirect immunoassays for determining whether a cell is producing IgM antibodies or to determine whether an antibody is of the IgM isotype. These assays involve incubating the cells with the monoclonal antibodies or labeled derivatives thereof. When the labeled derivatives are used, the presence of labeled binary immune complexes on the cells is read directly. When an unlabeled antibody is used, the cells are further incubated with a labeled antibody against the monoclonal antibody and the presence of labeled ternary immune complexes on the cells is read.

DETAILED DESCRIPTION OF THE INVENTION

Figure 1A:
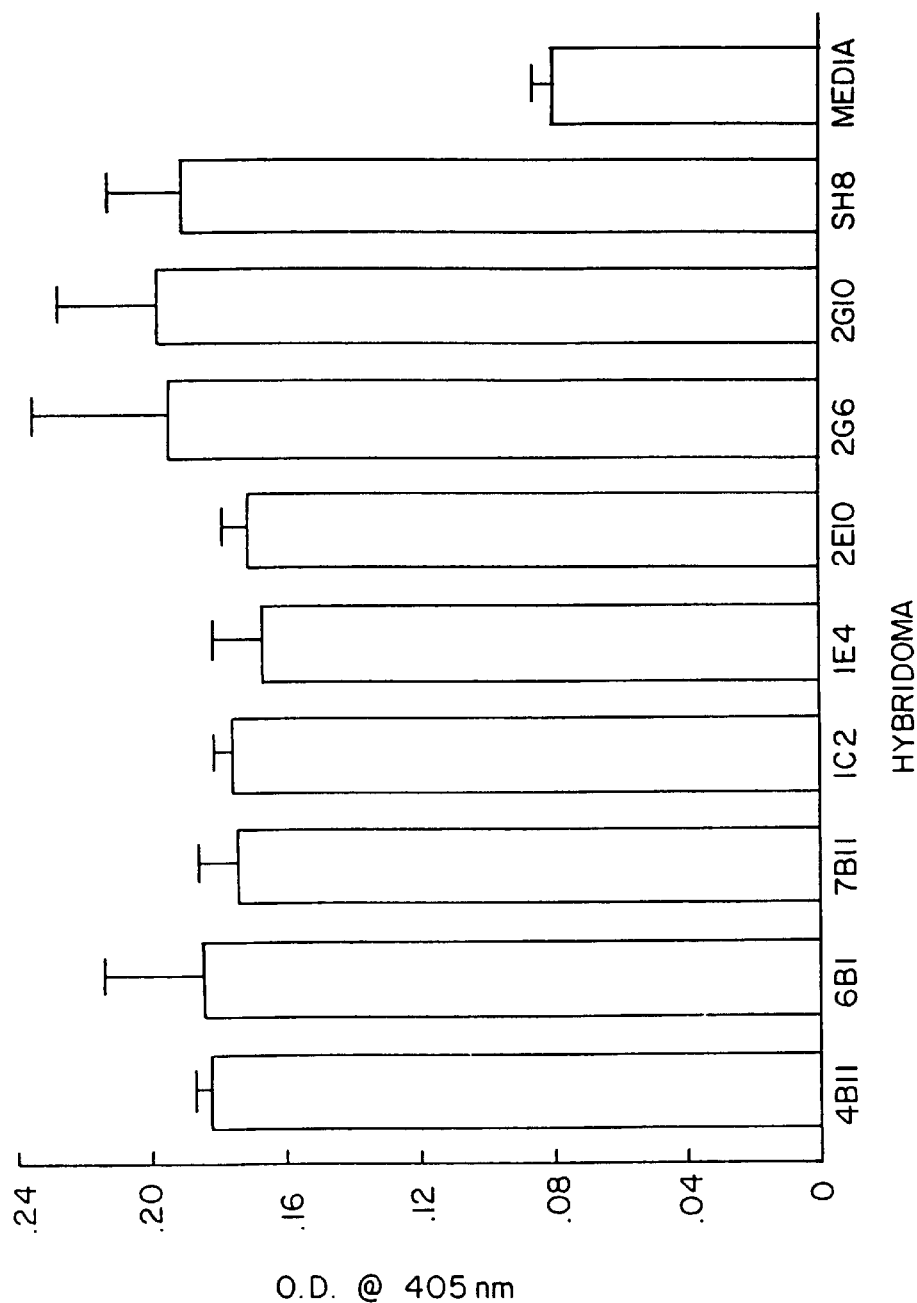
FIG. 1 demonstrates screening of hybridoma supernatants for IgM-specific antibody.

In order that the invention herein described may be more fully understood, the following detailed description is set forth.

As used herein the term "monoclonal antibody" means an antibody composition having a homogeneous antibody population. It is not intended to be limited as regards the source of the antibody or the manner in which it is made.

As used herein with respect to the exemplified rat monoclonal anti-murine IgM antibodies, the term "functional equivalent" means a monoclonal antibody that: (a) cross-blocks an exemplified monoclonal antibody; (b) binds selectively to murine IgM antibody; (c) has a G isotype; and (d) does not bind to $IgG_1$ or $IgG_2$ isotype.

As used herein with regard to the monoclonal antibody-producing hybridomas of the invention, the term "progeny" is intended to include all derivatives, issue, and offspring of the parent hybridoma that produce the monoclonal anti-murine IgM antibody produced by the parent, regardless of generation or karyotypic identity.

The present invention may be utilized to produce antibodies that will bind to IgM antibodies of any species. It is only necessary to utilize the teaching of the present invention to obtain a hybridoma cell line which is stable and continues to produce the anti-IgM antibody directed to the immunizing species. Preferably, the anti-IgM monoclonal antibody of the present invention is directed to a murine or human IgM.

Monoclonal Antibody Production

The antibody-producing fusion partners used to make the hybridomas of this invention are generated by immunizing rats with murine IgM antibody. The rats are inoculated subcutaneously and intraperitoneally with an immunogenic amount of the murine IgM antibody in Freund's adjuvant and then boosted with similar amounts of the immunogen in adjuvant. Spleens are collected from the immunized rats a few days after the final boost and a cell suspension is prepared therefrom for use in the fusion.

Hybridomas are prepared from the splenocytes and a rat tumor partner using the general somatic cell hybridization technique of Kohler, B. and Milstein, C., Nature (1975) 256: 495–497 [as modified by Buck, D. W., et al, In Vitro (1982) 18: 377–381]. Available rat myeloma lines, such as YB2/0 and Y3-Ag 1.2.3, may be used in the hybridization. Basically, the technique involves fusing the tumor cells and splenocytes using a fusogen such as polyethylene glycol. After the fusion, the cells are separated from the fusion medium and grown in a selective growth medium, such as HAT medium, to eliminate unhybridized parent cells. The hybridomas are expanded, if desired, and supernatants are assayed for anti-murine IgM activity by conventional immunoassay procedures (e.g., radioimmunoassay, enzyme immunoassay, or fluorescence immunoassay) using the immunizing agent $IgG_1$, $IgG_2$ and IgM (murine IgM antibody) as antigen.

Positive clones are characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, the conventional immunoglobulin purification procedures such as ammonium sulfate precipitation, gel electrophoresis, dialysis, chromatography, and ultrafiltration, if desired.

Monoclonal Antibody Selection/Characterization

The important characteristics of the monoclonal antibodies are (1) their immunoglobulin class, (2) their selectivity for murine IgM antibody, and (3) their usefulness in identifying and binding to murine IgM producing hybridoma cells.

The selectivity and range of a given antibody are determined by testing it against panels of (1) $IgG_1$, $IgG_2$ and IgM producing hybridoma cells and (2) $IgG_1$, $IgG_2$ and IgM antibodies. In selecting the claimed antibodies approximately 162 growing hybridoma cultures were initially screened. Nine clones reacted with the murine IgM antibody but not IgG. One of these clones was chosen for further characterization.

Antibodies exhibiting acceptable selectivity and range were conjugated to gelonin using N-succinimidyl-3-(2-pyridyldithio) propionate (SPDP) or iminothiolane (IT) as a coupling agent. The conjugates were tested against IgM and IgG coated plates to determine if specificity of the antibody is preserved after chemical coupling to the toxin.

Further details of the characterization of this antibody are provided in the examples below.

Immunochemicals

The immunochemical derivatives of the monoclonal antibodies of this invention that are of prime importance are immunotoxins (conjugates of the antibody and a cytotoxic moiety and labeled (e.g., radiolabeled, enzyme-labeled, magnetic-labeled or fluorochrome-labeled) derivatives in which the label provides a means for identifying and/or sorting immune complexes that include the labeled antibody.

The cytotoxic moiety of the immunotoxin may be a cytotoxic drug or an enzymatically active toxin of bacterial or plant origin, or an enzymatically active fragment ("A chain") of such a toxin. Enzymatically active toxins and fragments thereof are preferred and are exemplified by gelonin, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytoiacca americana* proteins (PAPI, PAPII, and PAP-S), momordica charantia inhibitor, curcin, crotin, saponaria officinalis inhibitor, mitogellin, restrictocin, phenomycin, and enomycin. Gelonin is most preferred. Conjugates of the monoclonal antibody and such cytotoxic moieties may be made using a variety of bifunctional protein coupling agents. Examples of such reagents are SPDP, IT, bifunctional derivatives of imidoesters such as dimethyl adipimidate—HCl active esters such as disuccinimidyl suberate, aldehydes such as glutaraldehyde, bis-azido compounds such as bis(p-azidopenzoyl) hexanediamine, bis-diazonium derivatives such as bis-(p-diamoniumbenzoyl)-ethylendiamine, diisocyanates such as tolylene 2,6-diisocyanate, and bis-active fluorine compounds such a 1,5-difluoro-2, 4-dinitrobenzene.

When used to kill murine IgM antibody producing hybridomas in vitro, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques to determine the presence or degree of IgM producing hybridoma cells.

When used in vivo for suppression of IgM producing cells, the immunotoxins are administered to the immunized animals in therapeutically effective amounts (i.e., amounts that eliminate or reduce the IgM producing splenocytes). They will normally be administered parenterally, preferably intravenously. The dose and dosage regimen will depend upon the nature of the IgM producing cell to be suppressed, the characteristics of the particular immunotoxin, e.g., its therapeutic index, and onset of action. The amount of immunotoxin administered will typically be in the range of about 0.1 to about 10 mg/kg of body weight.

For parenteral administration the immunotoxins will be formulated in a unit dosage injectable form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The immunotoxin will typically be formulated in such vehicles at concentrations of about 1 mg/ml to 10 mg/ml.

Cytotoxic radiopharmaceuticals for eliminating IgM producing hybridoma cells may be made by conjugating high linear energy transfer (LET) emitting isotopes (e.g., $^{98}$y, $^{95}$Pt) to the antibodies. The term "cytotoxic moiety" as used herein is intended to include such isotopes.

The labels that are used in making labeled versions of the antibodies include moieties that may be detected directly, such as fluorochromes and radiolabels, as well as moieties, such as enzymes, that must be reacted or derivatized to be detected. Examples of such labels are $^{32}$P, $^{125}$I, $^{3}$H, $^{14}$C, fluorescein and its derivatives, rhodamine and its derivatives, dansyl, umbelliferone, luciferia, 2,3-dihydrophthalazinediones, horseradish peroxidase, alkaline phosphatase, lysozyme, and glucose-6-phosphate dehydrogenase. The antibodies may be tagged with such labels by known methods. For instance, coupling agents such as aldehydes, carbodiimides, dimaleimide, imidates, succinimides, bis-diazotized benzadine and the like may be used to tag the antibodies with the above-described fluorescent, chemiluminescent, and enzyme labels. The antibodies may also be labeled with magnetic beads for use in magentic sorting regimens.

The antibodies and labeled antibodies may be used in a variety of cell sorting procedures to separate the IgM producing hybridoma cells from IgG producing hybridoma cells or to eliminate the IgM producing hybridoma cells from cultures containing such cells.

Common assay techniques that may be used include direct and indirect assays. Direct assays involve incubating a hybridoma or antibody of unknown isotype with a labeled antibody of the presnt invention. If the sample includes IgM producing cells, the labeled antibody will bind to those cells. After washing the cells to remove unbound labeled antibody, the sample is read for presence of labeled immune complexes. In indirect assays the cell sample is incubated with unlabeled monoclonal antibody. The sample is then treated with a labeled antibody against the monoclonal antibody (e.g., a labeled anti-rat antibody), washed, and read for the presence of labeled ternary complexes.

For diagnostic use or assays to determine the presence of IgM isotype the antibodies will typically be distributed in kit form. These kits will typically comprise the antibody in labeled or unlabeled form in suitable containers, reagents for the incubations and washings, labeled anti-rat antibody if the kit is for an indirect assay, and substrates or derivatizing agents depending on the nature of the label. IgM antigen controls and instructions may also be included.

The following examples provide a detailed description of the preparation, characterization, and use of a representative monoclonal antibody of this invention. These examples are not intended to limit the invention in any manner.

EXAMPLE 1

Characterization of Rat anti-Mouse IgM Monoclonal Antibodies

A rat hybridoma designated 58.6 was obtained from Dr. Joanne Trial, Department of Immunology, M. D. Anderson Cancer Center. Originally, the 58.6 cell line secreted a rat antibody. The cell line was not stable and, after about four subcultures, the 58.6 cells ceased producing any antibody. An original stock of cells was then cloned by limiting dilutions to obtain a cell line that would be stable and continue producing anti-IgM antibodies.

A) Cloning by limiting dilution 58.6 cells were cultured in Iscove's medium for 3 days at 37° C. in a humidified atmosphere of 5 $CO_2$ in air. When the expanded cell culture had reached 50% confluency, cells were harvested by centrifugation and counted using a hemacytometer. Cells were diluted in 50% fresh medium and 50% conditioned medium (medium in which 58.6 cells had been grown in for 7 days) and plated at approximately one cell per well into 96 well plates. When wells containing single cells had grown to small colonies (approximately 12 days), the medium was removed and assayed for anti-IgM antibody as described in Example 2. Positive cells were expanded for large scale production of antibody, freezing of cell stocks, and further characterization of the antibody. When cell lines were fully characterized for the type and specificity of antibody produced, appropriate cell lines were recloned and expanded for freezing of cells stocks and injections into pristane-treated nude mice for production of ascites fluid.

B) Freezing of hybrid cells

When hybrid cells plated into T75 flasks had reached 70% confluency, cells were collected by centrifugation and the pellet was resuspended in 0.9 ml of fetal bovine serum. Immediately before freezing, the cells were transferred to freezing vials and 0.1 ml of dimethyl sulfoxide was added to each vial. The vials were stored in liquid nitrogen.

C) Ascites fluid production

Approximately $10^7$ hybridoma cells were washed in serum-free media and injected intraperitoneally into nude mice which had received an intraperitoneal injection of 0.5 ml of pristane 7 to 14 days earlier. Ascites fluid usually formed within 1–3 weeks and was collected from the peritoneal cavity using a large gauge needle. Fluid was collected into tubes containing 5 ml of PBS with 20 mM EDTA. After centrifugation at 2000×g for 10 minutes, the supernatant was saved, made 0.1% in sodium azide, and stored at 4° C. or frozen at −20° C. in small aliquots. This fluid provided a rich source of monoclonal antibody (approximately 5–10 mg/ml).

EXAMPLE 2

Hybridomas Producing Anti-mouse IgM Antibodies

Hybridoma colonies which grew to a density of approximately 500–1000 cells within 2 weeks were chosen for further analysis in order to determine which of the hybridoma cells produced antibodies which bound murine IgM antibody. Hybridoma culture medium from these colonies was assayed for the presence of rat anti-mouse IgM by the Enzyme-linked immunosorbent assay (ELISA) performed. Basically, 100 ng of purified mouse IgM or IgG protein (sigma Chemical Company, St. Louis, Mo.) was diluted into coating buffer (50 mM $NaHCO_3$, pH 9.8) and absorbed overnight onto 96-well microtiter plates by incubation at 4° C. in a humidified chamber. The wells were then washed three times with phosphate-buffered saline containing 0.2% Tween-20 (PBS-Tween). After washing and removal of all traces of liquid in the wells by tapping lightly onto paper towels, 100 μl of hybridoma supernatant was added to the IgM-coated wells and incubated at room temperature for 2 hours. Plates were again washed with PBS-Tween, and incubated for one hour at room temperature with 100 μl of a 1:1000 dilution of peroxidase conjugated goat anti-rat IgG in PBS-Tween. After the wells were washed again as described above, they were reacted with 100 μl of 1 mM ABTS (2,2-azino-di(3-ethylbenzthiazoline sulphonic acid) in 0.1 M sodium citrate buffer pH 4.2, containing 0.03% hydrogen peroxide) for 20–60 minutes at 37° C. Optical density was measured at 405 nm on a MicroElisa Reader.

Figure 1B:
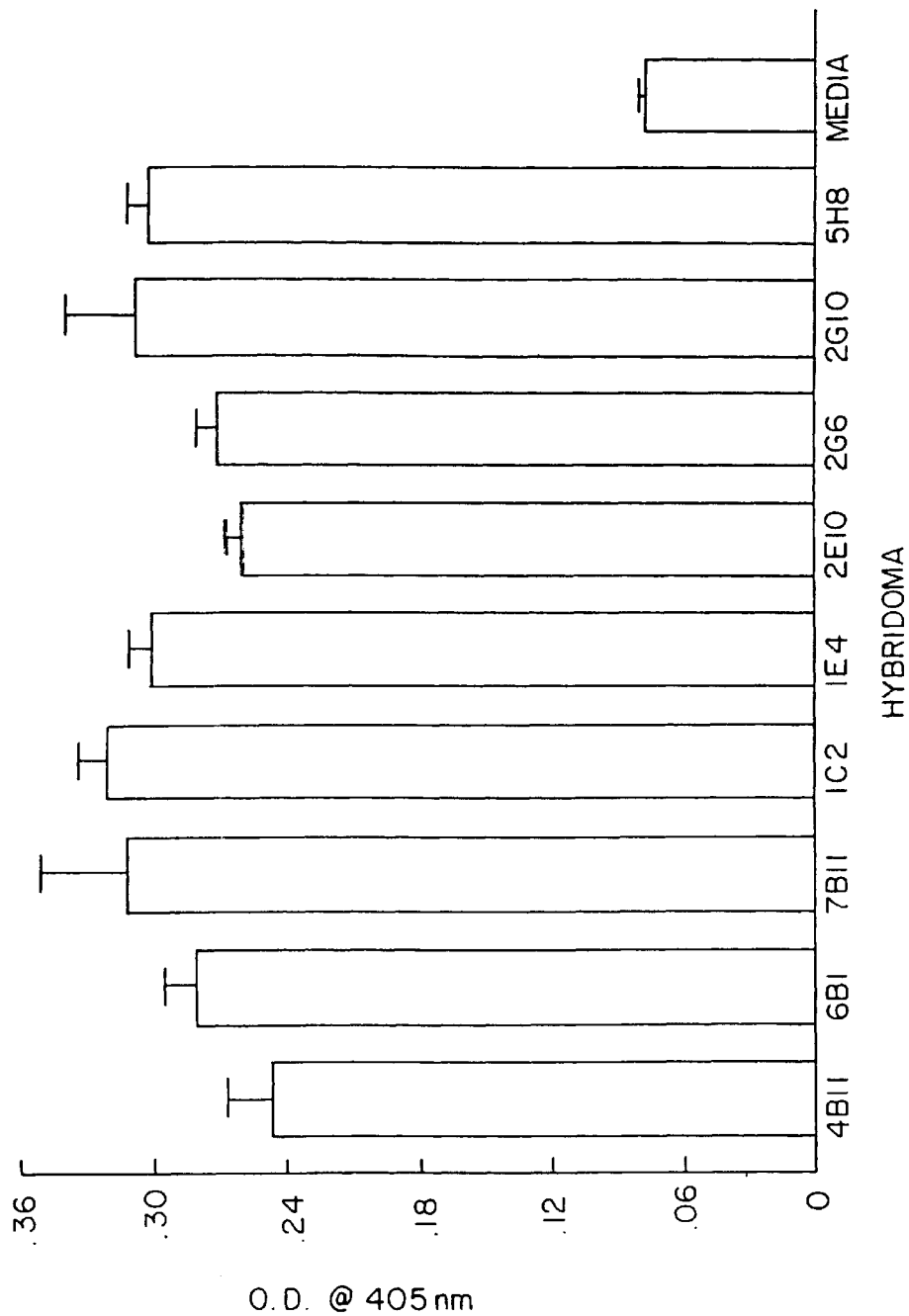

In order to assess whether the epitope recognized by the anti-IgM antibodies were on the heavy chain or light chain of the antibody, the binding of 9 hybridoma supernatants to IgM lambda and IgM-kappa protein coated plates was tested. Hybridomas IC2 and 2G10 both bound equally well to IgM-kappa and IgM-lambda coated wells, indicating that the binding specificity of the anti-IgM antibodies was on the heavy (mu) chain of the IgM antibody. That the other 7 antibodies tested also bound to murine IgM is indicated by the results shown in FIG. 1. As can be seen in FIGS. 1A and 1B, nine different hybridomas were tested against either IgM-kappa or IgM-lambda coated plates. A standard ELISA assay was performed to measure rat immunoglobulin bound to each plate. All antibodies were found to bind to both IgM-kappa and IgM-lambda coated wells. Among the highest binding antibodies, 1C2 and 2G10 were chosen for further study. Because of its growth and antibody production characteristics, antibody 2G10 was finally selected. This gave an optical density of 0.3±0.03 (standard deviation). The background was 0.06 optical density units (O.D.) using media without rat monoclonal antibody. Colonies producing antibody that gave a reaction on the anti-murine IgM antibody of greater than or equal to 0.3 O.D. were saved.

Figure 2:
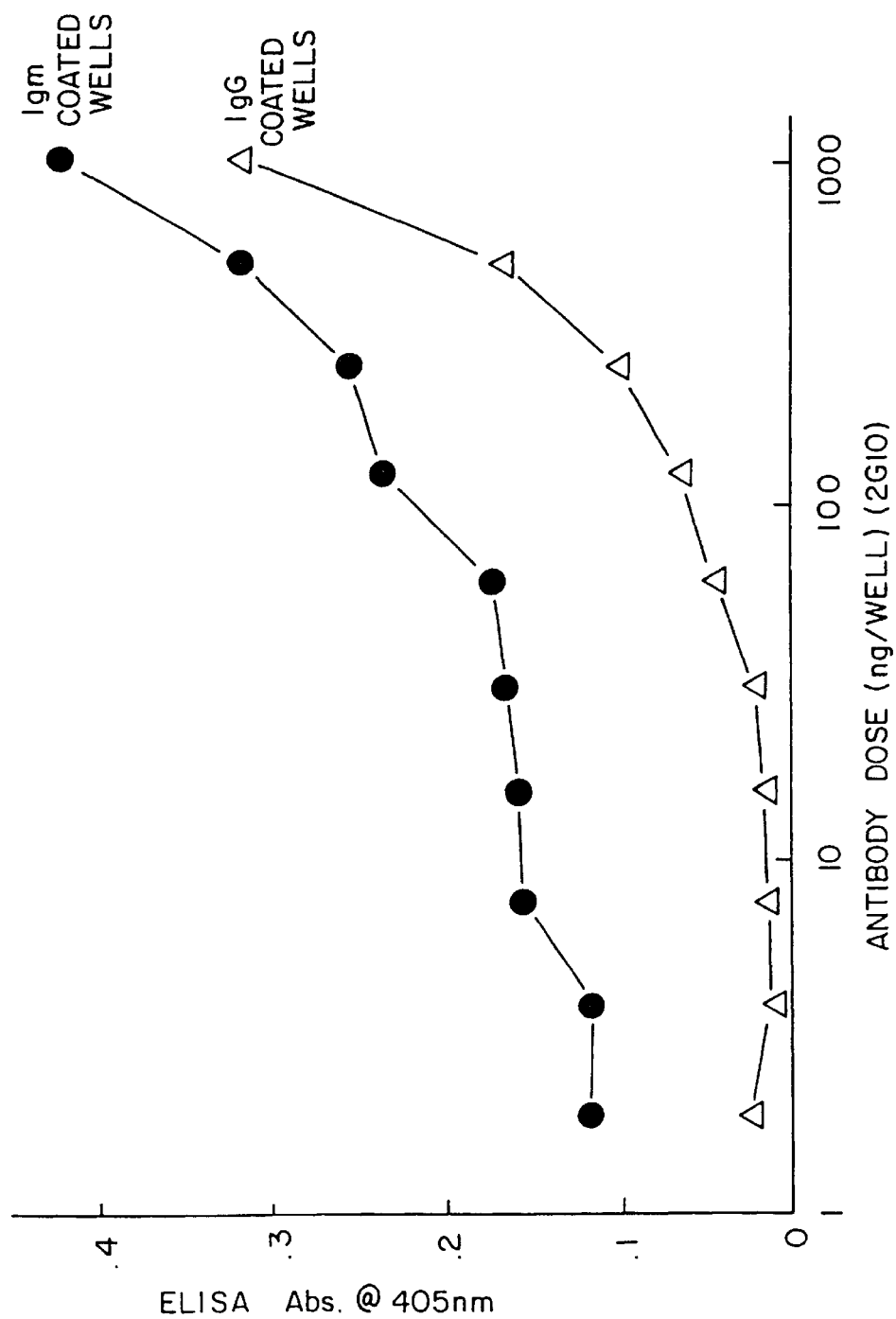
FIG. 2 demonstrates the dose-dependent specific binding of antibody 2G10.
Figure 3:
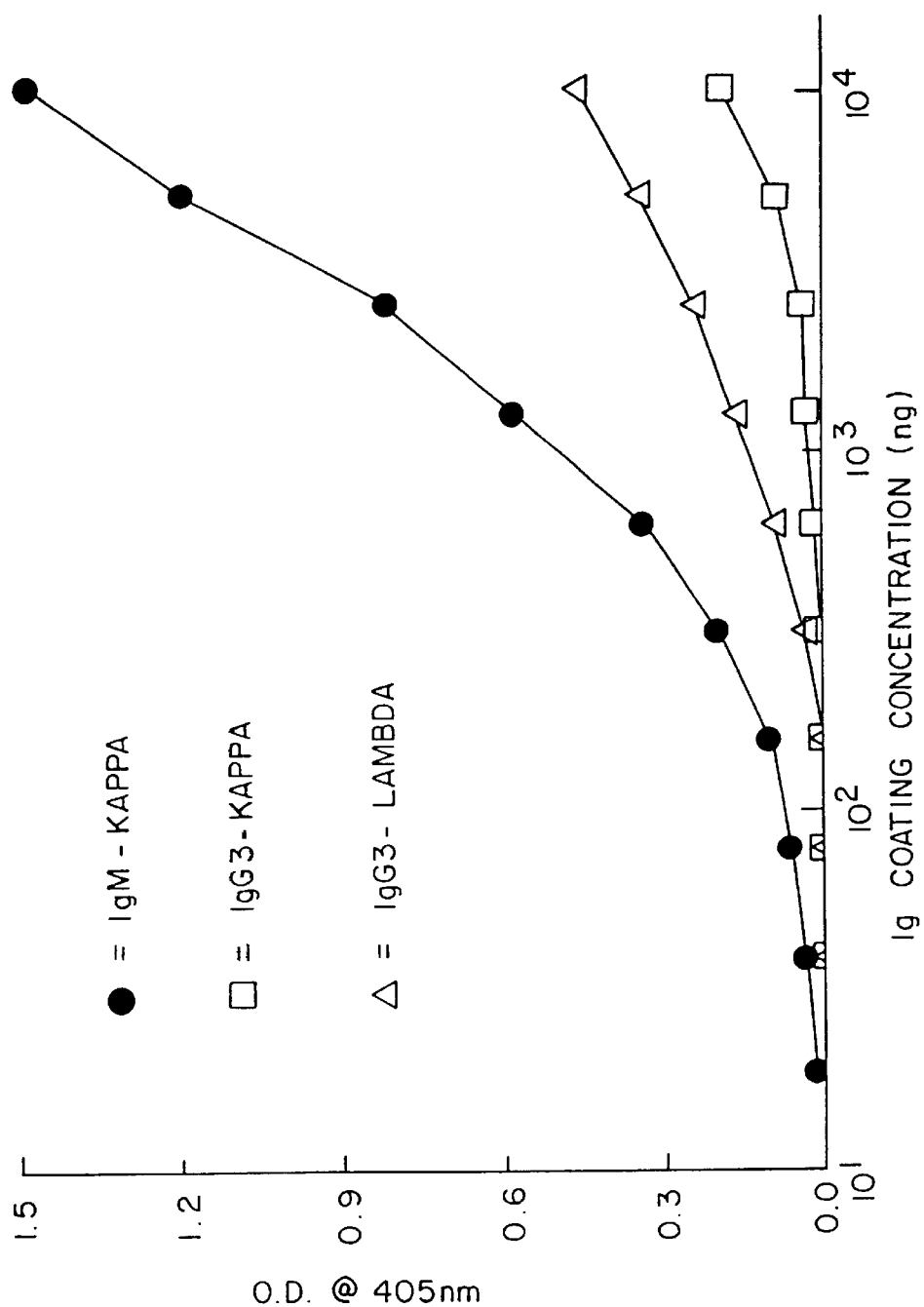
FIG. 3 demonstrates the effect of increasing absorbed murine immunoglobulin content on 2G10 binding.

The specificity of the rat monoclonal 2G10 antibody was tested by ELISA under a variety of conditions. To determine the selective recognition of IgM versus IgG by 2G10 100 ng of mouse IgM-lambda protein or $IgG_3$-lambda protein was absorbed onto microtiter plates (100 μl) and incubated with increasing concentrations of 2G10 antibody. As shown in FIG. 2, in the antibody dose range of 2–1000 ng, the 2G10 bound to IgM-coated microtiter plates to a greater extent than that achieved in IgG-coated plates. At 2G10 antibody doses of 50 ng and below, no binding was measurable on IgG-coated plates whereas IgM-coated wells were recognized by 2G10. The effect of increasing immunoglobulin coating concentration on microtiter plates and recognition by antibody 2G10 was also examined. As shown in FIG. 3, 2G10 antibody (added at a dose of 100 ng in 100 μl) incubated in IgG3 and IgM-coated wells shows a selective binding to IgM-coated plates at all coating concentrations. Ten-fold greater reactivity was measureable by ELISA on IgM-versus IgG-coated plates at a coating dose of 10000 ng of IgM or IgG (compare IgG3-kappa to IgM-kappa). The 2G10 antibody again demonstrated selective IgM binding.

Figure 4:
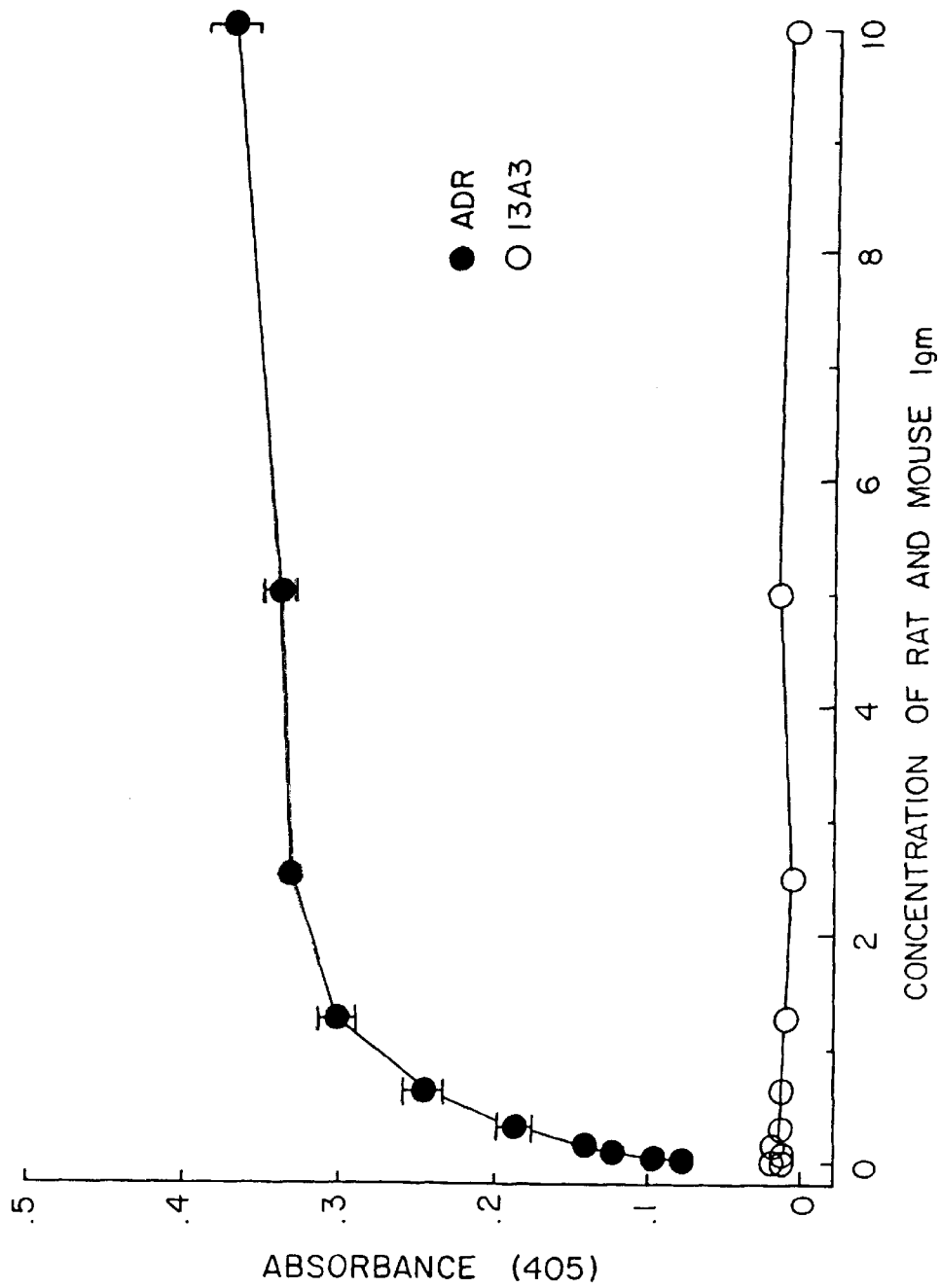
FIG. 4 shows selective recognition of murine IgM by 2G10 in an indirect ELISA.

Antibody 2G10 was also tested for its ability to selectively recognize IgM in an indirect ELISA assay. Antigens were coated to microtiter plates and were incubated with hybridoma culture media which contained antibody which recognizes these antigens. Antibodies of the IgM and IgG1 subclass were used in this assay. After incubation of antigen-coated plates with their interacting antibody, increasing concentrations of rat 2G10 antibody were added to the wells and the binding of 2G10 was evaluated by ELISA. As shown in FIG. 4, 2G10 sensitively and selectively recognized IgM bound to its respective antigen (closed circles), but was unable to detect IgG (open circles) under the same conditions, although the presence of IgG1 could be easily detected with antibodies reactive with all mouse immunoglobulin subtypes. FIG. 4 demonstrates the selective recognition of mouse IgM subclass immunoglobulins by 2G10 rat monoclonal antibody. The rat monoclonal antibody was also able to recognize IgM antibody at picogram doses, demonstrating its high affinity of murine IgM antibody.

EXAMPLE 3

Characterization of Rat Anti-Mouse IgM Antibodies

Mouse immunoglobulin of various subtypes (IgM-kappa and lambda, $IgG_1$, $IgG_2$, and $IgG_3$) was coated on microtiter plates as in Example 2 and the binding of the rat anti-mouse IgM antibodies produced by the hybridoma cells which were positive in Example 2 were further characterized. All plates were read in a Bio-Tek ELISA plate reader at a wavelength of 405 nm. Absorbance (compared to controls) was used an an indication of the presence of antibody against mouse IgM.

EXAMPLE 4
Purification and characterization of 2G10 rat monoclonal antibody

A representative rat anti-mouse IgM monoclonal antibody, designated 2G10, was chosen for further characterization. As was shown in Example 3, the 2G10 antibody was positive for IgM kappa and lambda binding. The antibody was purified by centrifugation and ammonium sulfate fractionation.

The representative hybridoma cell line designated 2G10 was deposited with the American Type Culture Collection (ATCC), Rockville, Md., U.S.A., on Apr. 23, 1990 and assigned Deposit Accession No. HB 10436. The deposits are available pursuant to the patent laws and regulations of the United States and of those countries foreign to the United States in which counterparts of this application are filed. The availability of the deposit does not constitute a license to practice the invention of this application in derogation of any patent issued thereon or on any division or continuation of this application.

2G10 culture supernatant (or ascites fluid from nude mice) was made 45% saturated in ammonium sulfate content (salting out) by the slow addition of an equal volume of 90% saturated ammonium sulfate solution. The sample was stirred for 30 minutes at 4 C. and then centrifuged at 20,000×g for 30 minutes. The pellet was resuspended in a 40% saturated ammonium sulfate solution, stirred 30 minutes and repelleted by centrifugation as described above. The pellet was resuspended in water and dialyzed against 100 volumes of PBS. Aliquots of the solution were used for determination of protein content (by optical density at 280 nm), purity (by SDS-PAGE) and binding specificity (by ELISA). The remaining antibody solution was frozen at −20° C. until needed.

Rat anti-IgM antibodies were purified by ammonium sulfate precipitation and gel filtration on a 2.6×40 cm column of chromatographic resin containing agarose, dextran and/or acrylamide eluting with PBS/0.01% sodium azide at room temperature at a flow rate of 1 ml/minute.

The subclass of 2G10 rat monoclonal antibody was determined by the method of Ouchterlony (ouchterlony and Nilsson (1958) in Handbook of Exp. Immun. Weir, ed., Blackwell Scientific, London, pp. 19.1–19.44) using an immunodiffusion kit commercially available through ICN Immunobiologicals, Lisle, Ill.

Figure 6:
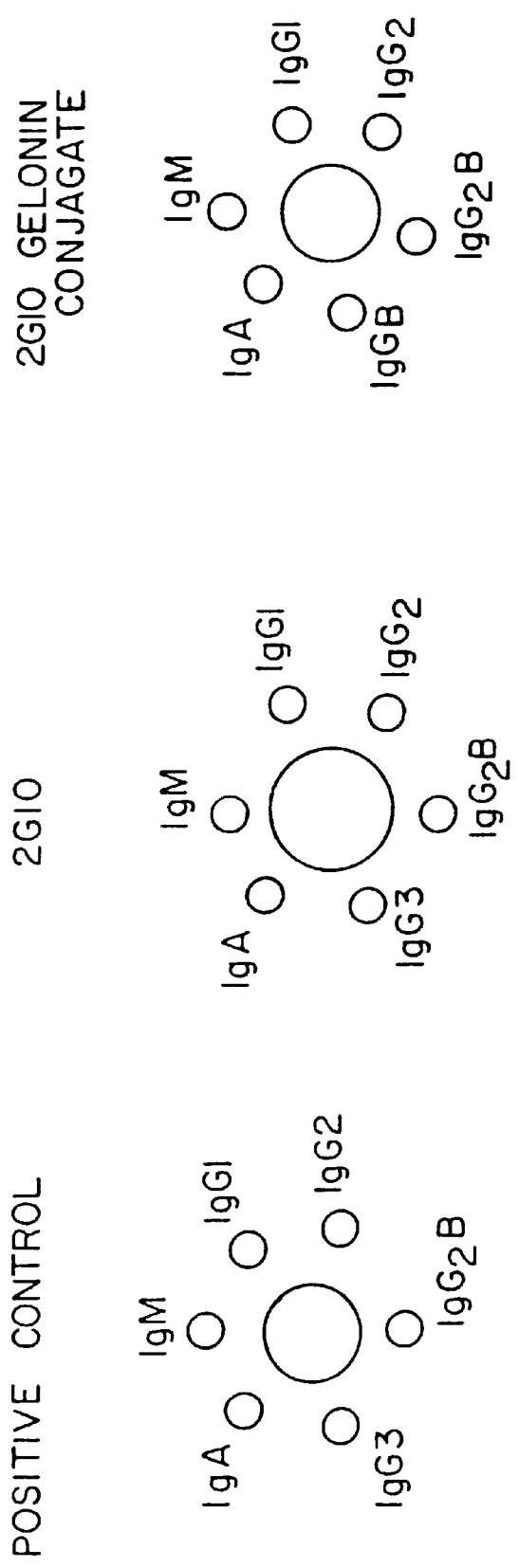
FIG. 6 characterizes the subclass of rat 2G10 antibody by Ouchterlony immunodiffusion.

The subclass of antibody 2G10 is important in evaluating how to purify this molecule. To perform subclass analysis, an Ouchterlony immunodiffusion technique kit was employed. Briefly, antisera against various rat immunoglobin sub-types was added to each of the satellite wells. In the center well, a known standard or unknown sample was added and allowed to diffuse into the semisolid media. A precipitation band at the site of the specific antisera indicates the subtype. As shown in FIG. 6, the positive control samples containing all rat sub-type antibodies show reaction lines at all of the sub-type wells. On the other hand, 2G10 antibody reacted only with the $IgG_2a$ sub-type antisera which designates that rat antibody 2G10 is an $IgG_2a$ antibody.

In order to evaluate the binding of a commercially-available rat antibody to mouse IgM, the ELISA reactivity of rat monoclonal antibody LO-MM-9 (from Serotec, cat#MCA 199) against murine IgM was evaluated. One hundred nanograms of mu-k, gamma-k, or gamma-1 was added to each well of a 96 well plate. Various ammounts of Lo-MM-9 rat antibody were then added and an ELISA assay for rat antibody was performed as described previously. As shown in Table 1, there was no binding of this rat antibody to murine IgM coating the wells.

TABLE I

Evaluation of rat antibodies against murine IgM

| | ELISA reactivity against murine Ig | | |
|---|---|---|---|
| Concentration | Mu-k | gamma-k | gamma-k |
| 1000 ng | 0.058 | 0.008 | 0.037 |
| 500 ng | 0.034 | 0.004 | 0.031 |
| 100 ng | 0.032 | 0.001 | 0.021 |
| 50 ng | 0.030 | 0.001 | 0.020 |
| 10 ng | 0.021 | 0.001 | 0.002 |
| 5 ng | 0.018 | 0.001 | 0.024 |
| 1 ng | 0.009 | 0.001 | 0.020 |
| 0.1 ng | 0.020 | 0.001 | 0.023 |

Figure 5:
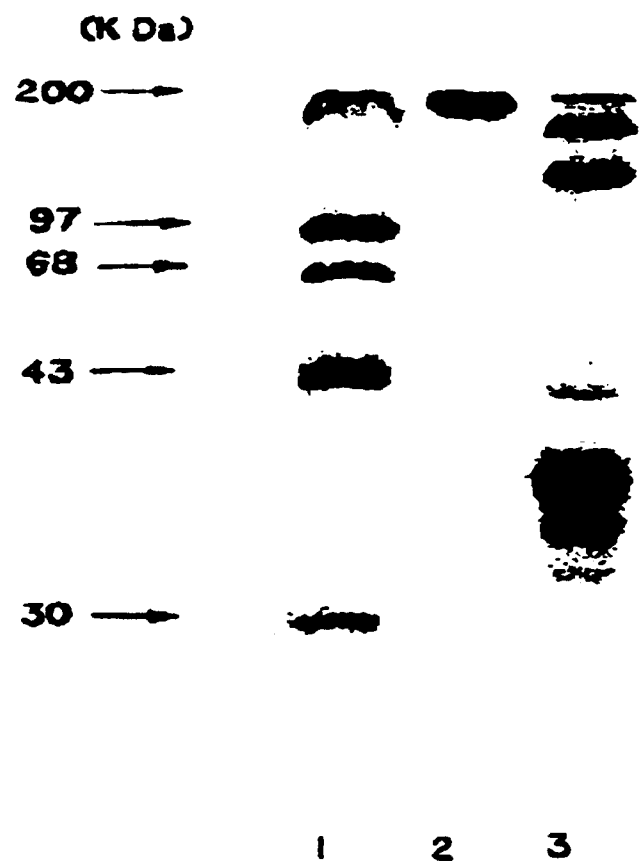
FIG. 5 illustrates the purity of 2G10 antibody by SDS-PAGE.

Thus, this antibody was not deemed useful for further study. In addition, as shown in FIG. 5, lane 3, this antibody preparation contained at least three major protein bands and at least five minor protein bands as assessed by SDS PAGE.

EXAMPLE 5
Binding of Rat Anti-Mouse IgM to IgM Producing Cells

In order to demonstrate that the 2G10 rat anti-mouse IgM antibody bound not only to purified IgM antibody coating a 96 well plate but also to cells producing an IgM antibody, FACS analysis was performed on 10C1 cells and murine 238-57 ADR hybridoma cells which secrete IgG and IgM, respectively. Briefly, $1 \times 10^6$ cells were centrifuged at 500×g for 3 minutes, washed three times with PBS and resuspended in 3 ml of PBS.

Fluorescein conjugated affinity purified $F(ab)_2$ fragment goat anti-mouse immunoglobin IgM (Cappel) was diluted 1:100 in PBS (1x) and 20–40 µl was added to a 20 µl cell suspension. After incubation for 15–20 minutes in the dark at room temperature, the cells were washed twice with PBS centrifuging at 500 rpm for 3 minutes.

An aliquot of 300 µl of paraformaldehyde (1% in PBS) was added to fix the cells. The cells were incubated at 4° C. until sorted by flow cytometry.

For indirect staining, hybridoma cells were first incubated with rat anti-mouse IgM antibody 2G10, washed, then stained with the fluorescein $F(ab)_2$ fragment goat anti-mouse immunoglobulin IGM and sorted by flow cytometry.

Figure 7A:
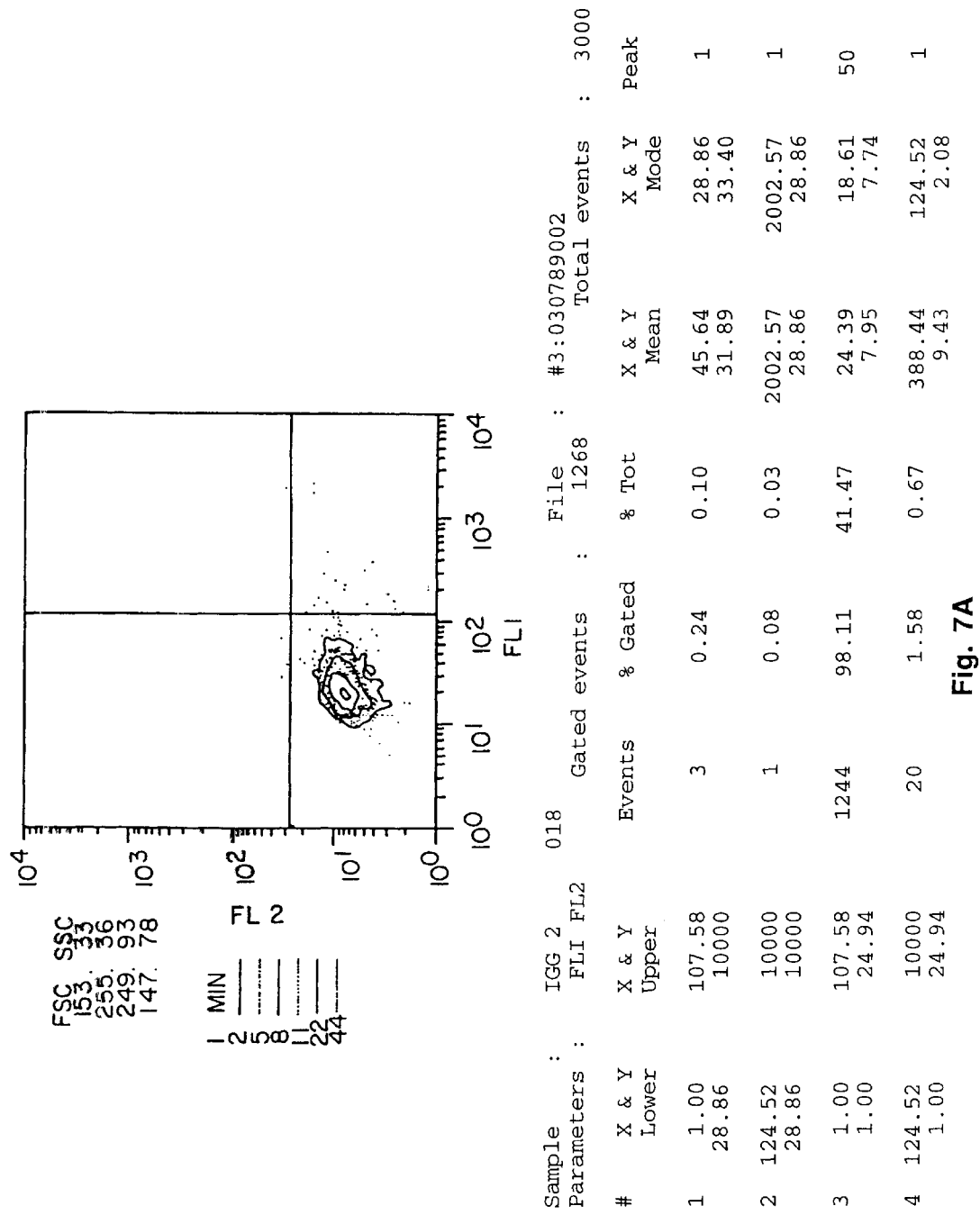
FIGS. 7A and 7B demonstrate utilization of 2G10 for binding to cells expressing IgM subclass antibodies.
Figure 7B:
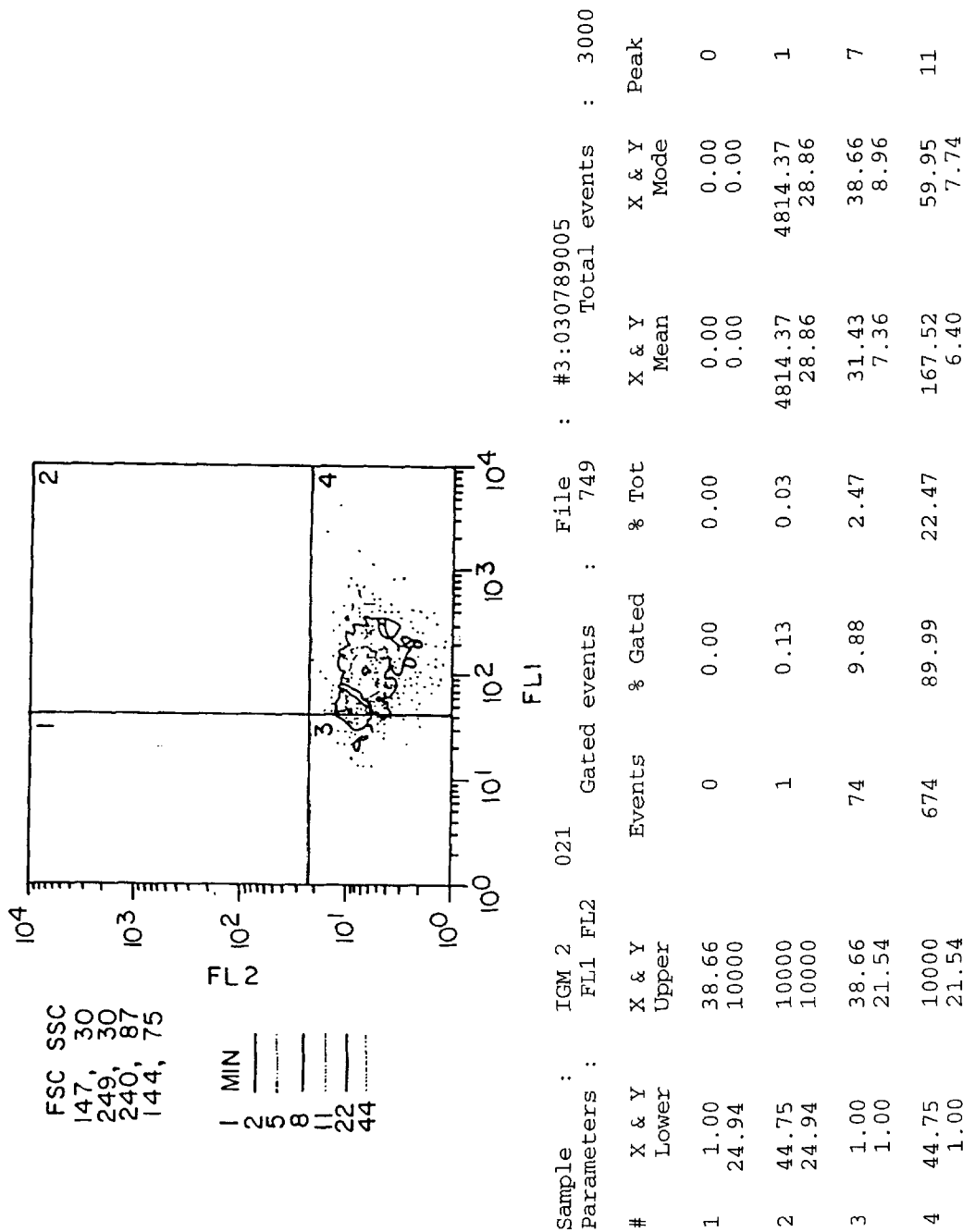

As shown in Table 2 and FIG. 7B, antibody 2G10 bound specifically to IgM present on the surface of IgM secreting murine hybridoma cells and not to IgG secreting cells.

TABLE II

FACS Analysis of IgM and IgG Expressing Murine Hybridoma Cells

| | % of Fluorescein-labeled cells | |
|---|---|---|
| TREATMENT | IgG HYBRIDS | IgM HYBRIDS |
| 0 | 0.87 | 0.37 |
| Irrelevant Rat IgG + FITC Goat Anti-Rat | 0.23 | 0.96 |
| 2G10 Rat Anti-Mouse IgM AbY + FITC Goat Anti-Rat | 1.58 | 89.99 |

As Table 2 shows, there was no background fluorescense of untreated cells. Irrelevant rat IgG also did not bind to either IgG hybrids or IgM hybrids. There was no binding of the 2G10 antibody to IgG producing hybridoma cells (1.58% of cells positive. FIG. 7A and Table 2). However, as shown in FIG. 7B and Table 2, 90% of cells producing murine IgM antibody were shown to bind strongly to the 2G10 antibody. Therefore, the binding of antibody 2G10 to cells occurs due to the recognition of the murine IgM on the cell surface.

It will be appreciated that the properties of the antibodies examined are effectively the only relevant characteristics of the corresponding hybridomas in that, for the purposes of the present invention, the hybridomas are characterized by their ability to produce particular antibodies having said properties.

EXAMPLE 6

Coupling of 2G10 to Gelonin

A stock solution of SPDP reagent (N-Succininidyl 3-(2-pyridylditho) proprionate) (6mg/ml) in dry DMF was prepared. To 1 ml of a PBS solution containing 1 mg of 2G10 antibody in a 12×75 mm glass test tube, SPDP was slowly added to a 5-fold molar excess (approximately 10 $\mu$l of stock solution). The mixture was vortexed every 5 minutes for 30 minutes at room temperature.

Excess unreacted SPDP was removed from the sample by gel filtration chromatography on a Sephadex G-25 column (1×24 cm) pre-equilibrated in 100 $\mu$mM sodium phosphate buffer pH 7.0 containing 0.5 mM EDTA (Buffer A). Fractions (0.5 ml) were collected and analyzed for protein content using the Bradford dye binding assay (Bradford, (1976) *Anal. Biochem.* 72: 248–254). Absorbance (600 nm) was monitored in a 96-well plate using a Bio-TEK Microplate autoreader. Antibody eluted at the void volume (fractions 14–20) and these fractions were pooled and kept at 4° C.

Gelonin toxin was extracted from the seeds of *Gelonium multiflorum* and purified to homogeneity utilizing the method of Stirpe, et al (Stirpe, et al., *J. Biol. Chem.* 255: 6947–6953 (1980)). One milligram of purified gelonin (2 mg/ml in PBS) was added to triethanolamine hydrochloride (TEA/HCl) buffer to a final concentration of 60 mM TEA/HCl and adjusted to pH 8.0. The solution was made 1 mM in EDTA concentration. 2-iminothiolane stock solution (0.5M in 0.5M TEA/HCl pH 8.0) was added to a final concentration of 1 mM and the sample was incubated for 90 minutes at 4° C. under nitrogen gas.

Excess 2-iminothiolane reagent was removed by gel filtration on a column of Sephadex G-25 (1×24 cm) pre-equilibrated with 5 mM bis-tris acetate buffer pH 5.8 containing 50 mM NaCl and 1 mM EDTA. Fractions (0.5 ml) were collected and analyzed for protein content in 96 well microtiter plates using the Bradford dye binding assay. Gelonin eluted in fractions 14–20 were pooled and stored at 4° C. SPDP-modified antibody 2G10 was mixed with a 5-fold molar excess of 2-iminothiolane modified gelonin. The pH of the mixture was adjusted to 7.0 by the addition of 0.05 M TEA/HCl buffer (pH 8.0) and the mixture was incubated for 20 hours at 40° C. under nitrogen. Iodoacetamide (0.1 M in PBS) was added to a final concentration of 2 mM to block any remaining free sulfhydryl groups and incubation was continued for an additional hour at 25° C.

Purification of 2G10 Gelonin Complexes

To remove low molecular weight products and non-conjugated gelonin, the reaction mixture was applied to a Sephadex S-300 column (1.6×31 cm) previously equilibrated with PBS. Fractions (1.0 ml) were collected and 50 $\mu$l aliquots were analyzed for protein content using the Bio-Rad dye binding assay. To remove unconjugated 2G10, the high molecular peak (fraction 17–233) from the S-300 column was applied to an affinity chromatography column of Blue Sepharose CL-6B (1×24 cm) pre-equilibrated with 10 mM phosphate buffer (pH 7.2) containing 0.1 M NaCl. After sample loading, the column was washed with 30 ml of buffer to completely elute non-conjugated antibody. The column was eluted with a linear salt gradient of 0.1 to 2 M NaCl in 10 mM phosphate buffer, pH 7.2. Protein content of the eluted fractions was determined by the dye-binding assay described previously.

Figure 8:
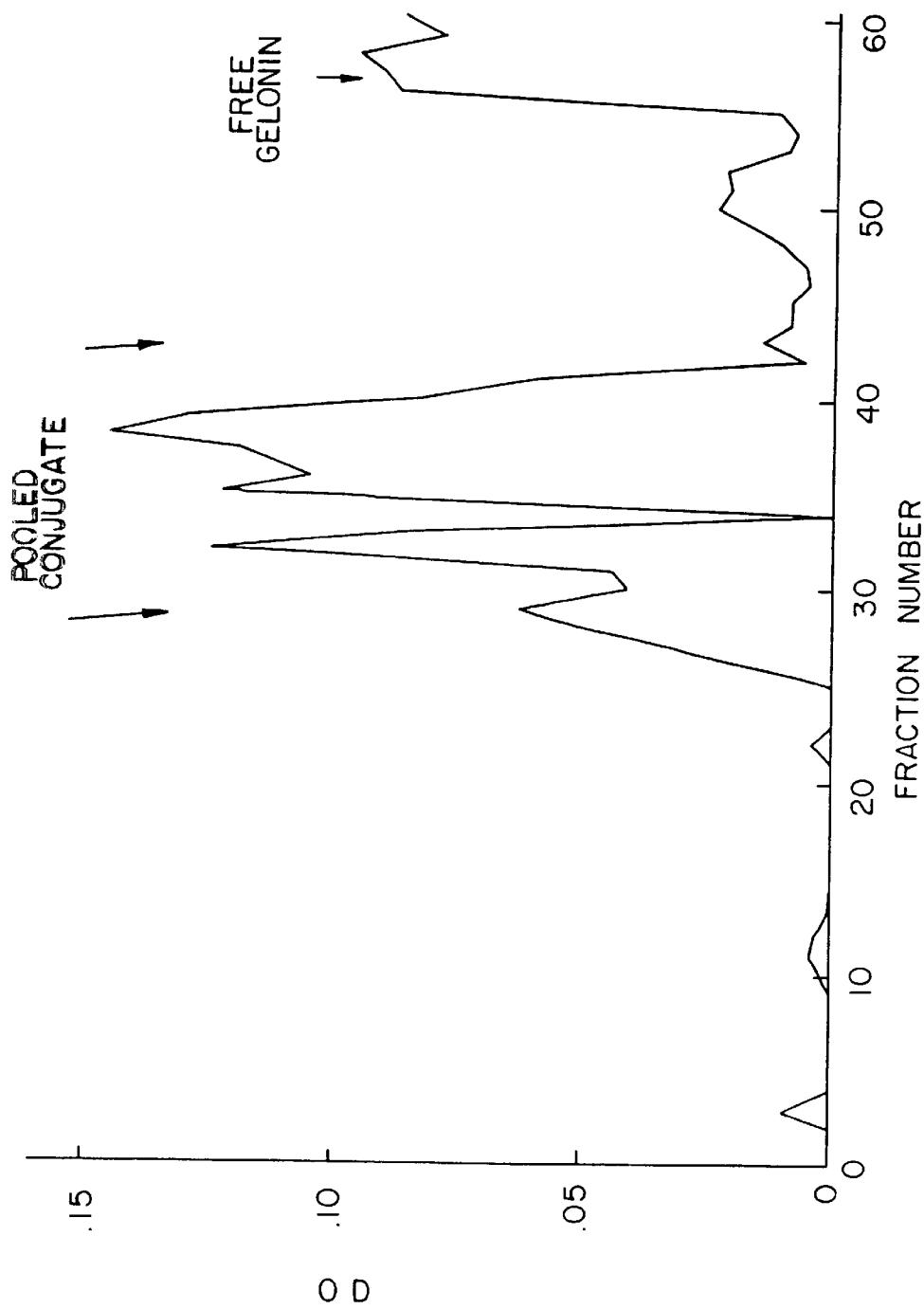
FIG. 8 illustrates the elution profile of immunotoxin (composed of 2G10 coupled to gelonin) on a gel filtration matrice.

The coupling mixture containing free 2G10 antibody, 2G10 gelonin and free gelonin was first purified by gel filtration on an S-300 column. As shown in FIG. 8, a high molecular weight peak was detected (fractions 25–42) as well as a lower molecular weight peak (fractions 55–67). Fractions 26–42 were pooled for analysis of conjugate purity and reactivity.

Figure 9:
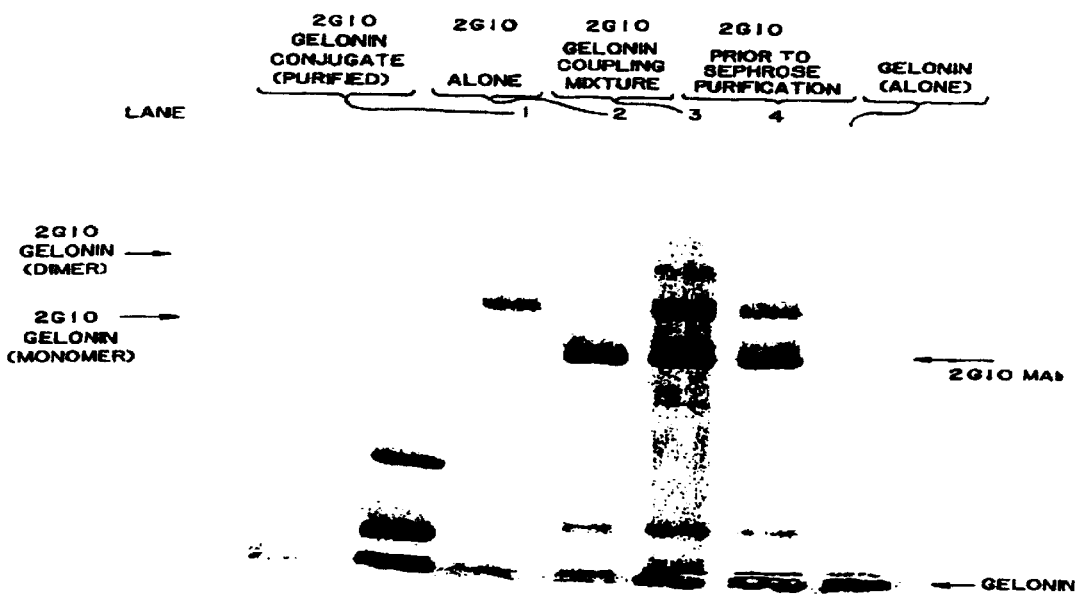
FIG. 9 demonstrates the purity of 2G10-gelonin immunotoxin by SDS-PAGE.

SDS-PAGE analysis of the purified 2G10 gelonin conjugate was performed. As can be seen in FIG. 9, the 2G10 gelonin coupling mixture (lane 3) contained free 2G10, free gelonin (arrows) as well as 2G10 coupled to 1 gelonin molecule (monomer, arrow) and 2G10 coupled to 2 gelonin molecules (dimer, arrow). As seen in lane 1, the final purified 2G10 gelonin conjugate contains mostly 2G10 coupled to 1 gelonin molecule and lesser amount of 2G10 coupled to 2 gelonin molecules. The preparation was not contaminated by free gelonin or free antibody.

Figure 10:
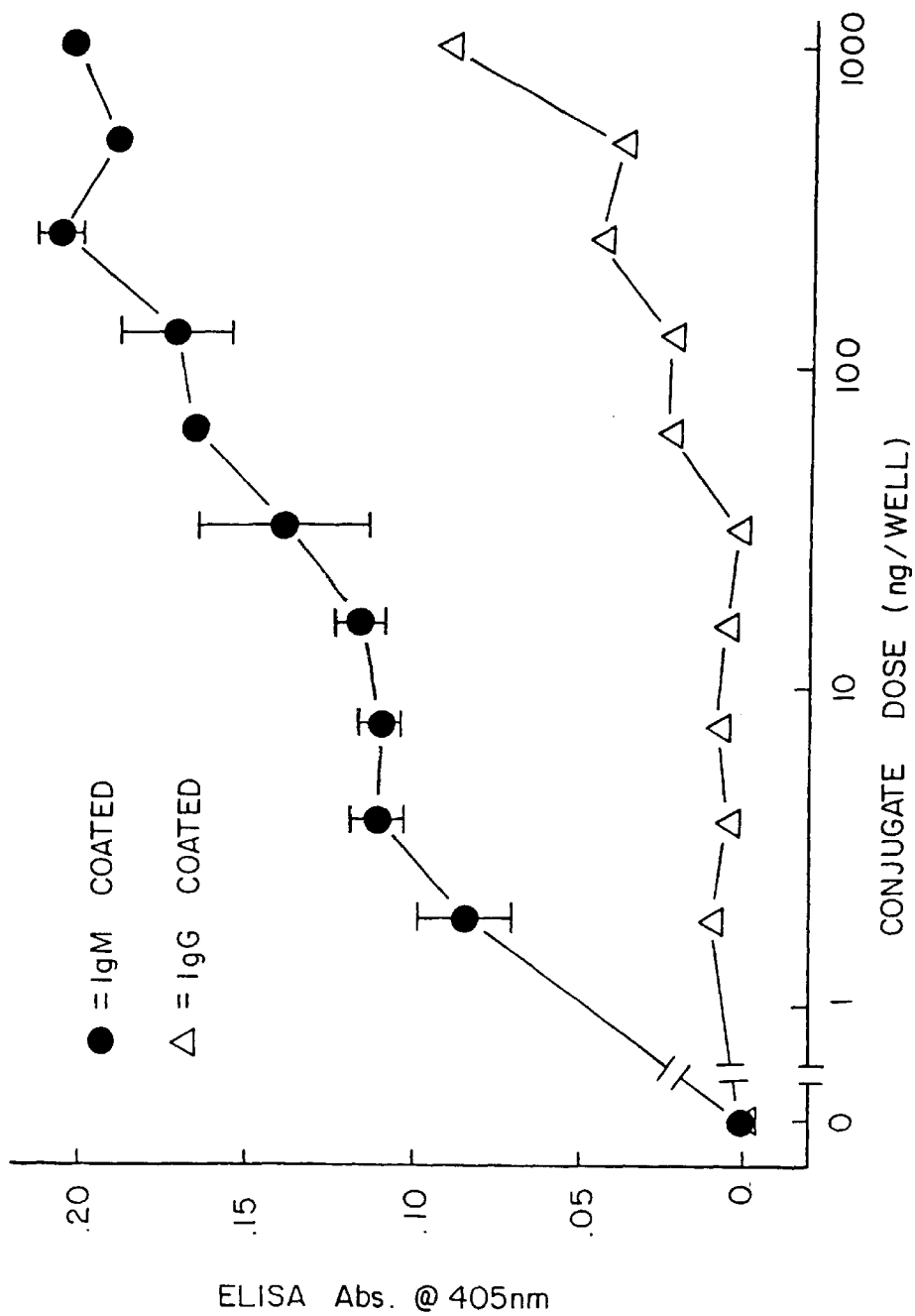
FIG. 10 shows the specific binding of immunotoxin (2G10-gelonin) to murine IgM.
Figure 11:
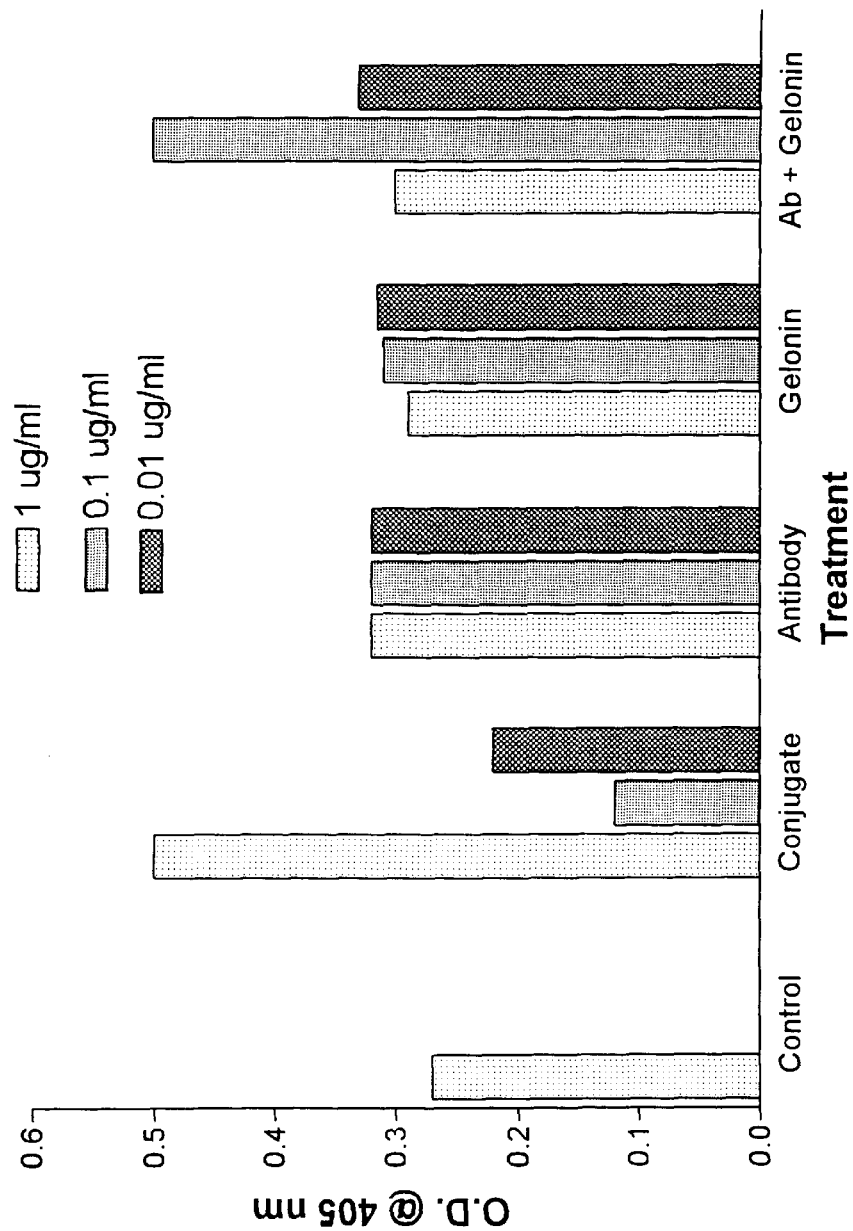
FIG. 11 shows the effect of treatment on IgM secretion from primary lymphocyte culture—after 24 hours I.
Figure 12:
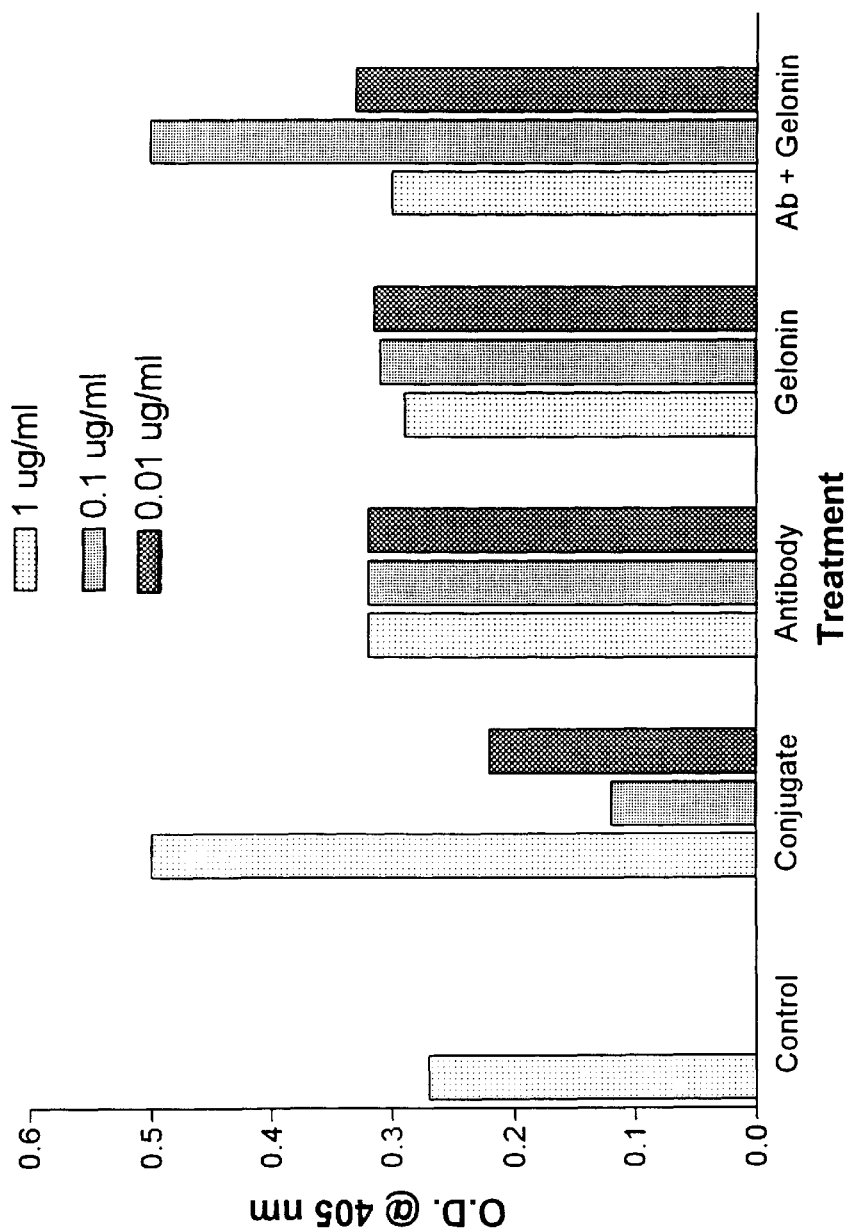
FIG. 12 shows the effect of treatment on IgM secretion from primary lymphocyte culture—72 hours I.
Figure 13:
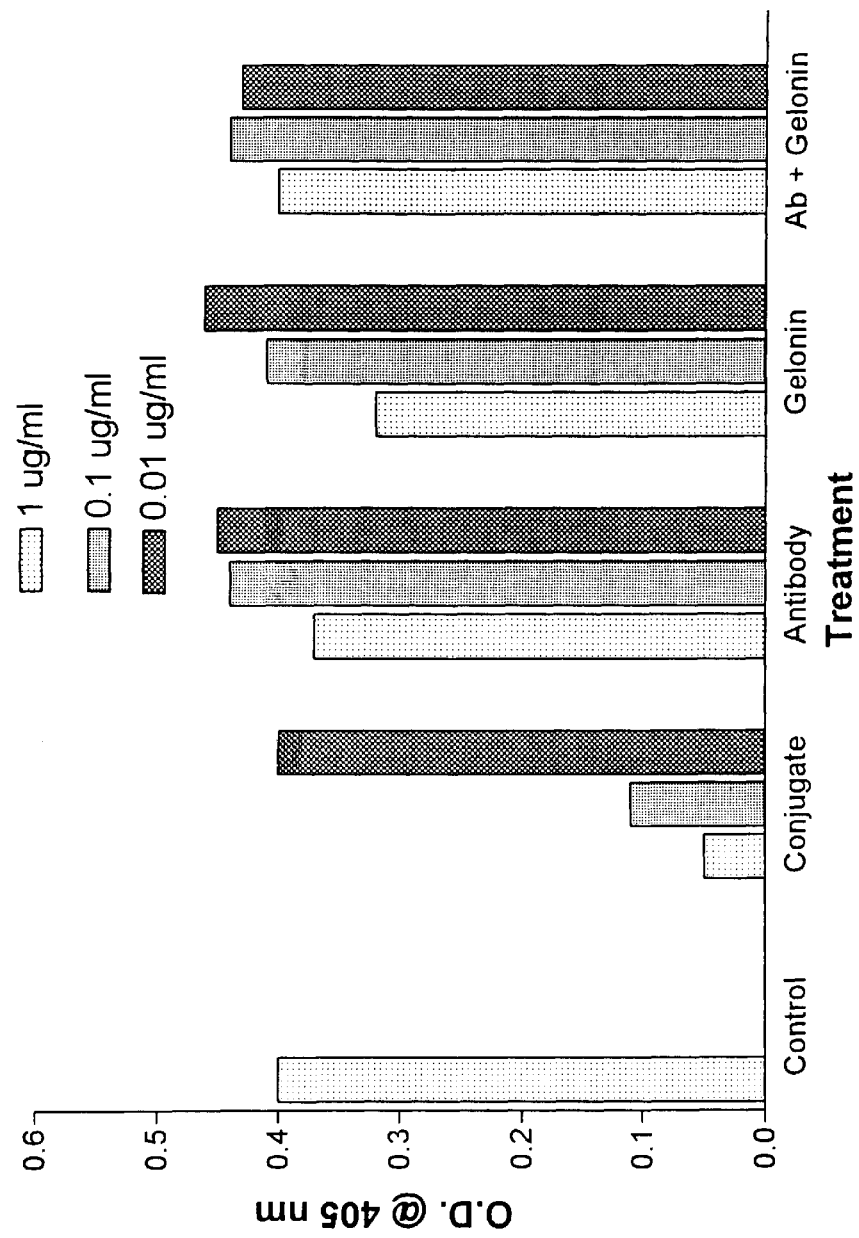
FIG. 13 shows the effect of treatment on IgM secretion from primary lymphocyte culture—96 hours I.
Figure 14:
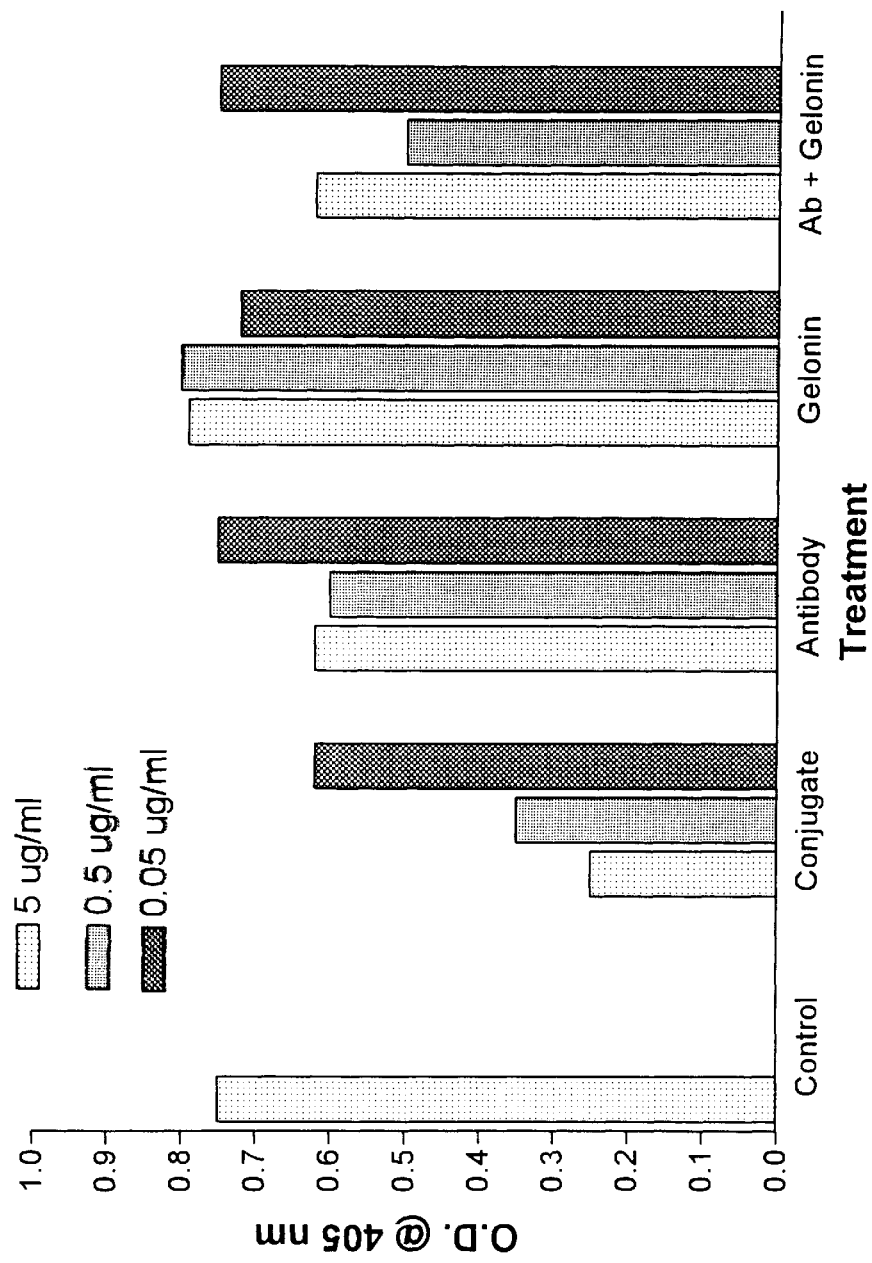
FIG. 14 shows the effect of treatment on IgM secretion from primary lymphocyte culture—24 hours II.
Figure 15:
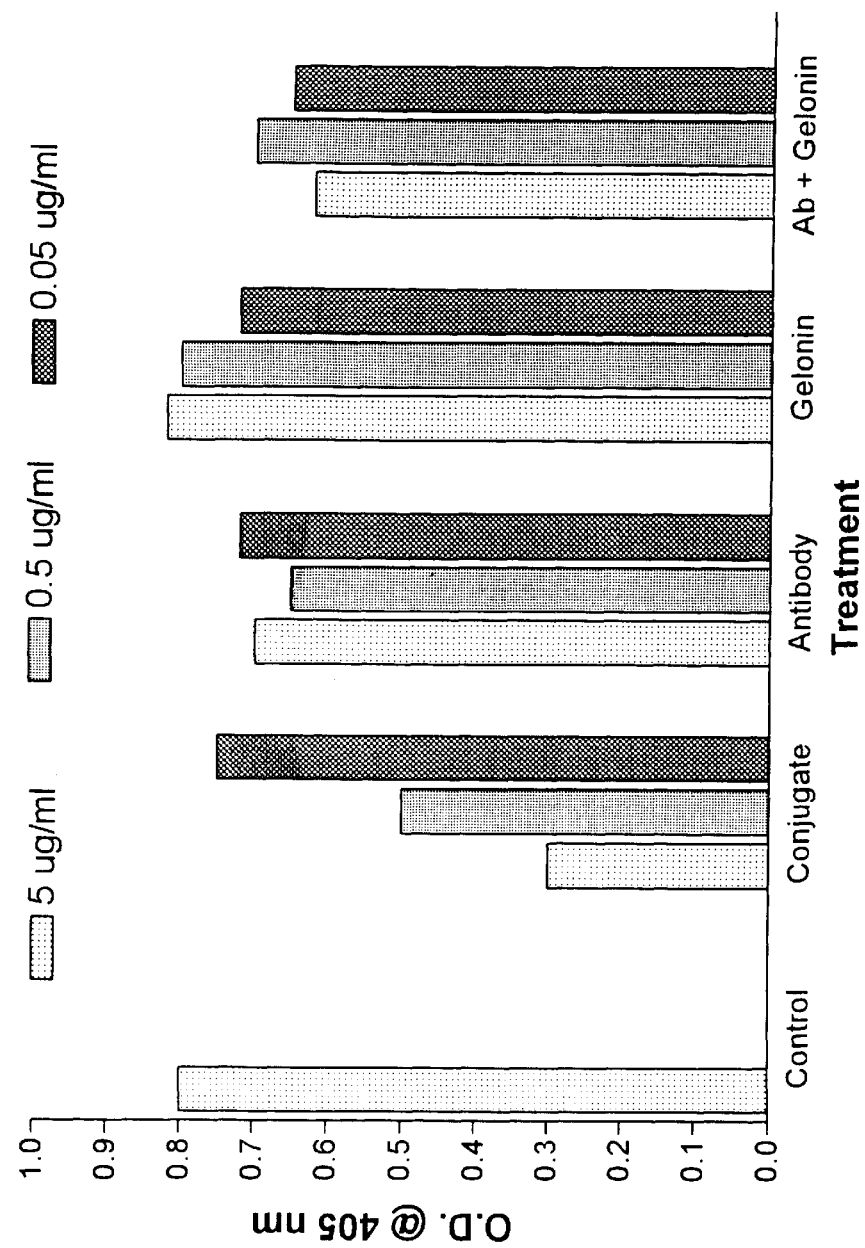
FIG. 15 shows the effect of treatment on IgM secretion from primary lymphocyte culture—48 hours II.
Figure 16:
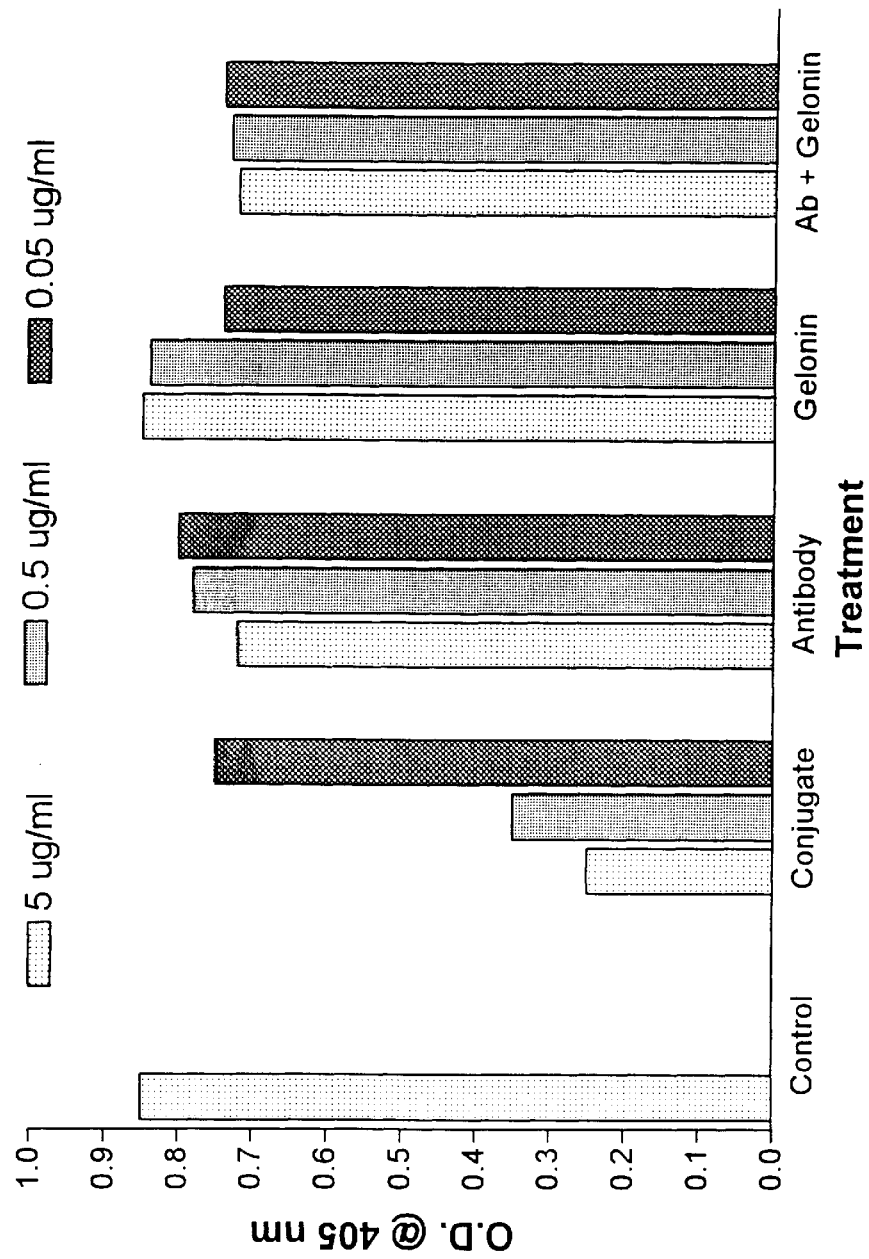
FIG. 16 shows the effect of treatment on IgM secretion from primary lymphocyte culture—72 hours II.
Figure 17:
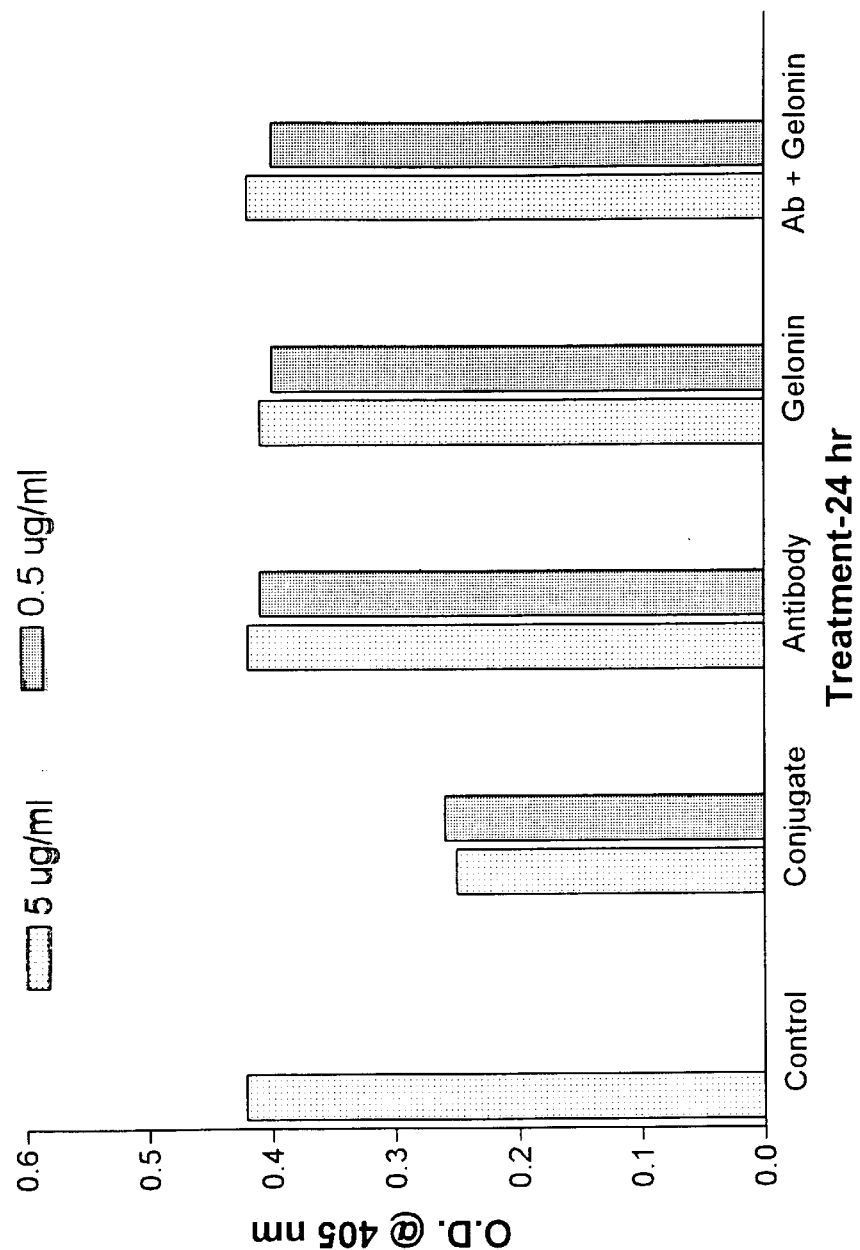
FIG. 17 shows the effect of 2 hour treatment on IgM secretion from primary lymphocyte culture—24 hours III.
Figure 18:
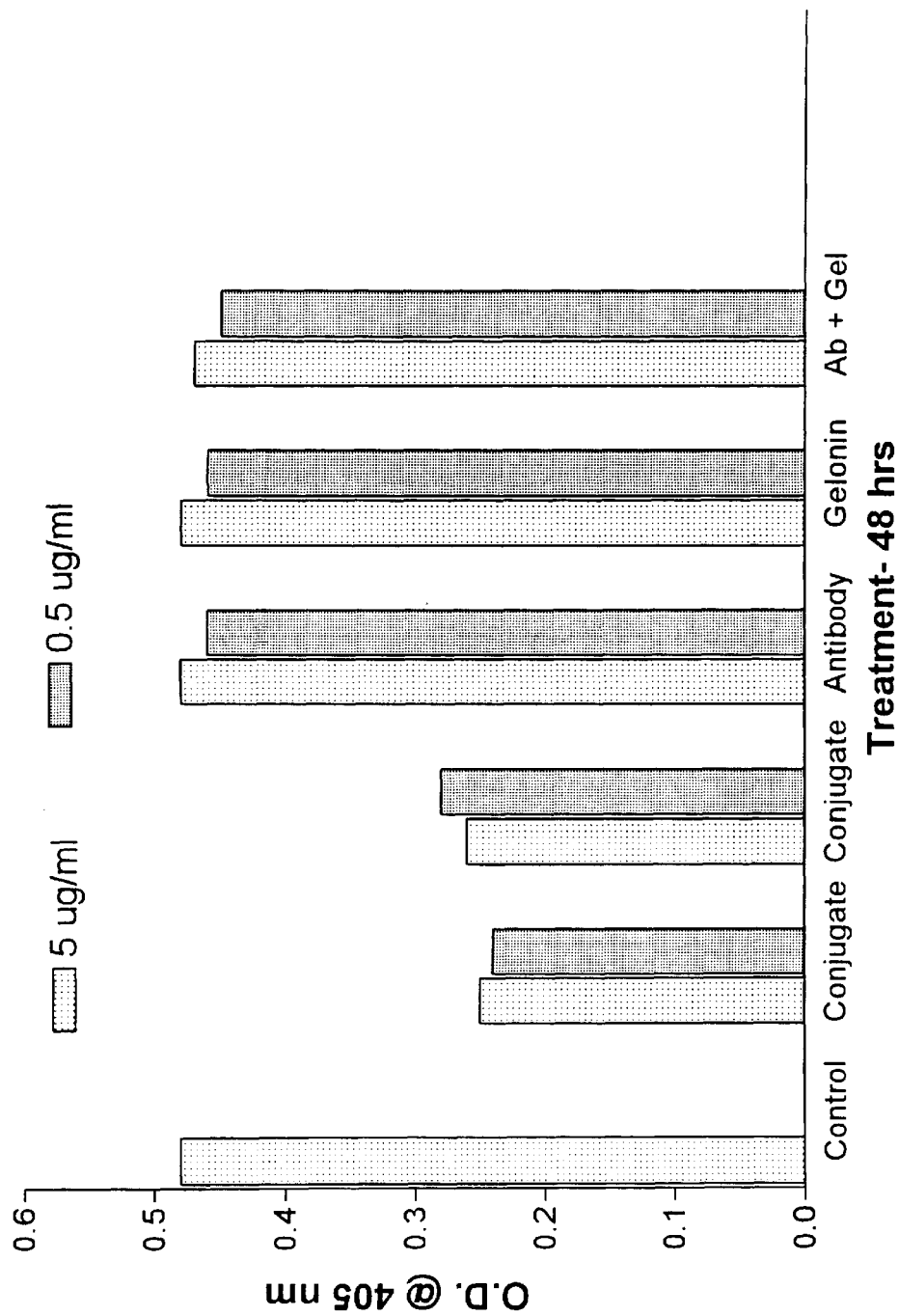
FIG. 18 shows the effect of 2 hour treatment on IgM secretion from primary lymphocyte culture—48 hours III.
Figure 19:
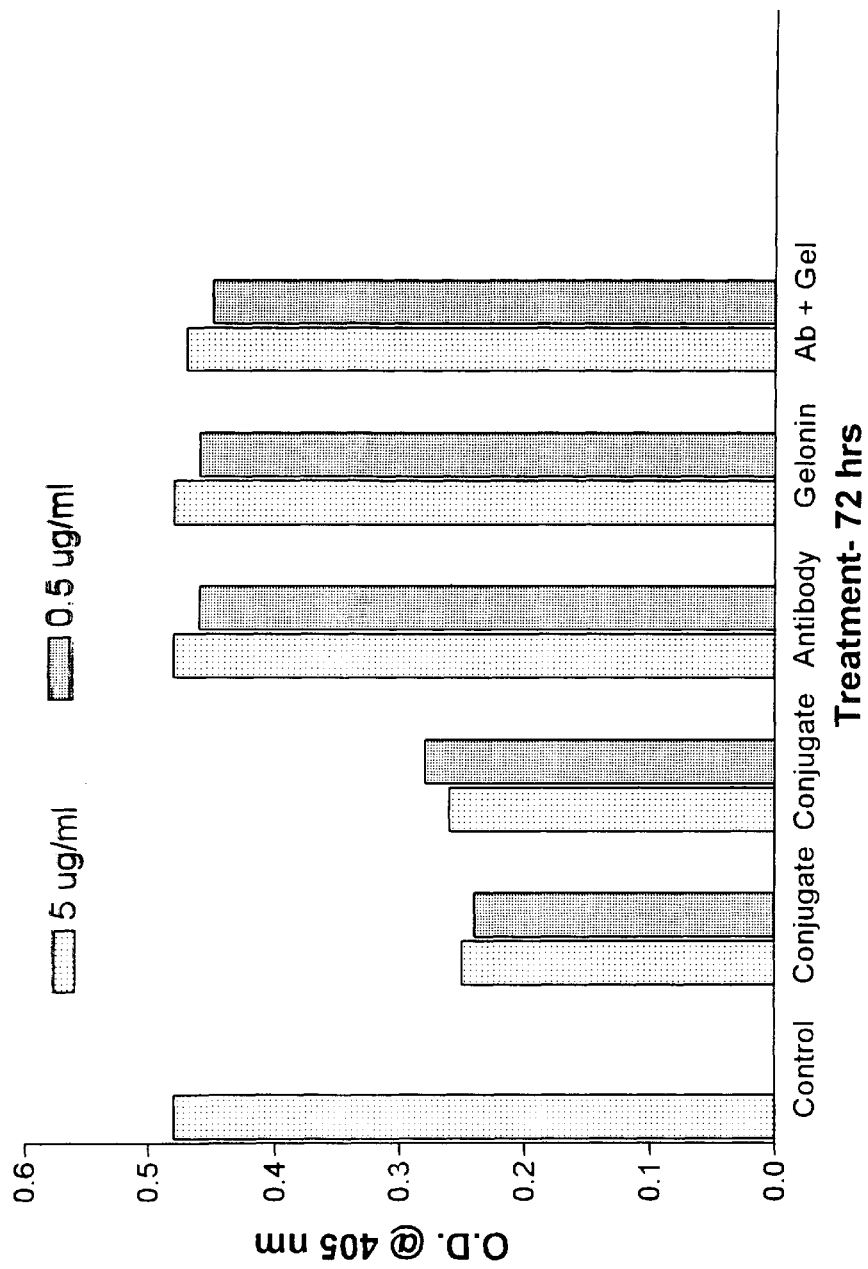
FIG. 19 shows the effect of 2 hour treatment on IgM secretion from primary lymphocyte culture—72 hours III.
Figure 20:
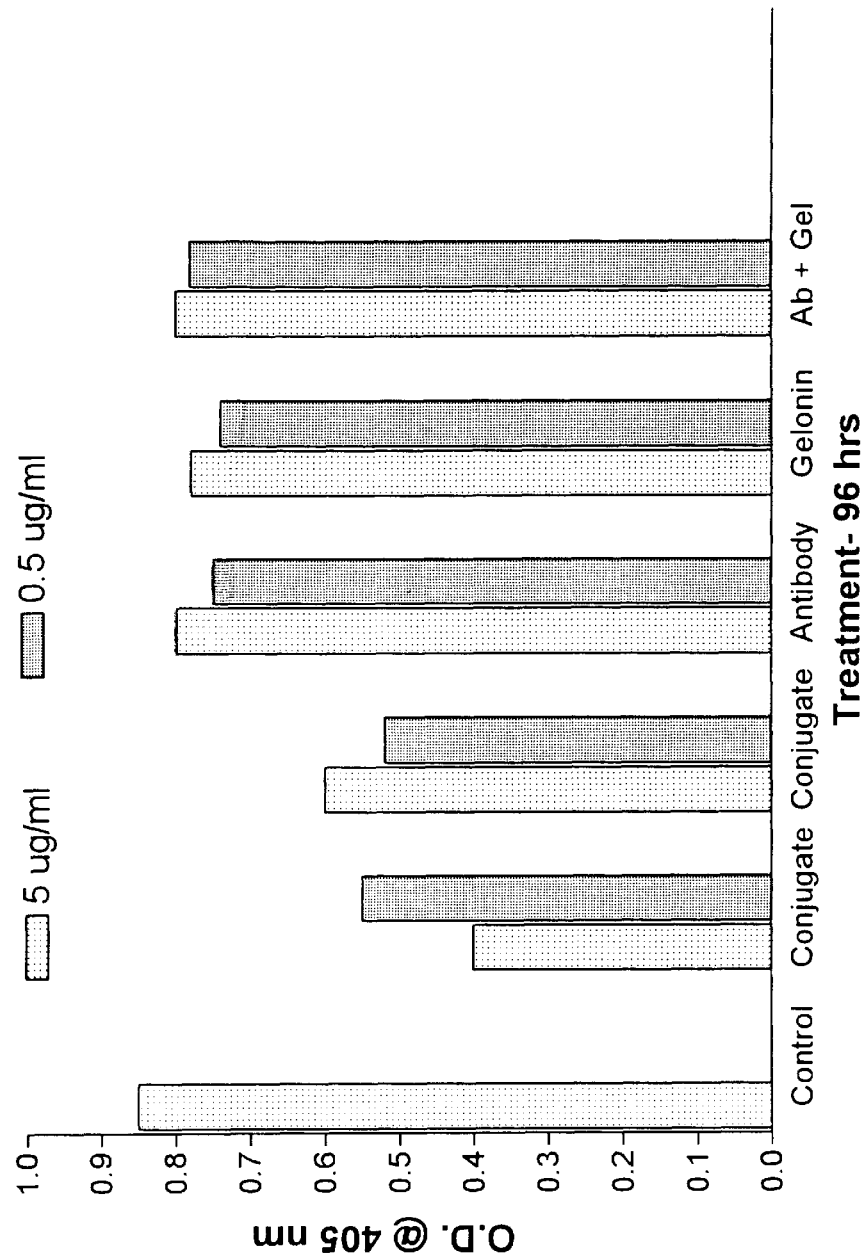
FIG. 20 shows the effect of 2 hour treatment on IgM secretion from primary lymphocyte culture—96 hours III.

To determine whether the chemical reaction and coupling of this 2G10 antibody to gelonin modified the recognition of the 2G10 antibody for murine IgM, 96 well plates were coated with either murine IgG or IgM antibody as in FIG. 2. Instead of 2G10 antibody, the 2G10 gelonin conjugate was added to wells at various concentrations. A standard ELISA assay was then performed to detect rat antibody. As shown in FIG. 10, the 2G10 gelonin conjugate bound readily to IgM and only to a small extent to IgG coated plates. Only at the highest concentration tested (1000 ng/well) did the 2G10 gelonin conjugate bind significantly to the IgG-coated wells. In contrast, at a similar concentration the 2G10 gelonin conjugate bound extensively to the IgM coated wells. Thus, the immunoreactivity of the 2G10 gelonin conjugate towards IgM was preserved. In addition, the 2G10 gelonin conjugate failed to cross-react appreciably with murine IgG and therefore the selectivity of the 2G10 gelonin conjugate was also unaltered. Thus, the 2G10 gelonin conjugate should bind to IgM expressed on murine cells in the same manner as that of antibody 2G10 itself.

EXAMPLE 7

Production of ODC Monoclonal Antibodies

A. In Vitro Immunization and Monoclonal Antibody Production

Protocols employed currently for the production of murine monoclonal antibodies result in the generation of hybridomas which secrete antibodies of the IgM subclass. In order to demonstrate the typical result of murine monoclonal antibody production protocols, two techniques were employed for generation of monoclonal antibodies against a rat protein, ornithine decarboxylase (ODC). The first technique involves immunization of murine spleen cells in vitro, i.e., in culture dishes, with ODC protein.

This technique was performed by the method of Luben (Luben and Mohler, (1980) *Molec. Immunol.* 17:635–639) using 25 $\mu$g of purified rat liver ODC. Briefly, ODC protein was incubated with mouse cells for 72 hours at 37° C. in the presence of thymocyte conditioned medium (a source of immunoglobulin secreting cell type specific growth factors). The spleen cells were then fused with MPC myeloma cells using polyethylene glycol as a fusogen. The resultant hybrid cells were tested for the secretion of antibody reactive with ODC protein. The results are shown in Table III.

TABLE III

In Vitro Immunization and Hybridoma Production Summary

| | Production Summary | Remarks |
|---|---|---|
| Total wells plated | 48 | Two 24-well plates. 1 × 10⁶ cells/well |
| Total wells with viable hybrids/Total wells plated | 48/48 | Represents a minimum fusion frequency of 1:10⁶ |
| Total wells positive by first ELISA | 48/48 | 14 of these were greater than 4-fold above control media in ELISA |
| Wells positive for ODC activity precipitation/wells tested | 12/14 | Only the 14 most positive in ELISA were tested |
| Total wells expanded for cloning | 12/48 | Limited to the 12 most promising clones |
| Total individual ELISA positive monoclones recovered from 12 original polyclonal wells | 70 | As few as one recovered from polyclonal well and as many as 18 |
| Total monoclonals positive for ODC activity precipitation/Total assayed | 50/70 | AS much as 48% of the added OD activity precipitated and as little as 4% |
| Total monoclones secreting IgM/total monoclones | 70/70 | |
| Total monoclones secreting IgG/total monoclones | 0/70 | |

After initial screening with ODC protein, the hybridomas were recloned and retested. Seventy hybridomas were obtained which reacted with the ODC protein by several criteria. However, as shown in Table III, all of the clones were secreting IgM isotype antibodies. None were secreting IgG antibodies. These antibodies were found to be of limited use in a variety of applications for monoclonal antibodies.

B. In Vivo immunization and Monoclonal Antibody Production.

A second technique employed for the production of monoclonal antibodies was the immunization of a mouse by injection with purified ODC protein. Mouse spleen cells were isolated after immunization, fused with P3×63 Ag 8.653 myeloma cells (utilizing PEG as described above). Clones were isolated, tested for reactivity with ODC protein and further characterized for utilization as a specific ODC recognizing reagent.

TABLE IV

In vivo immunization and Intraspecies Hybridoma

| | Production Summary | Remarks |
|---|---|---|
| Total wells plated | 1200 | Numerous wells of 96-well plates plated with 2.5 × 10³ cells/well |
| Total wells with viable colonies | 148 | Approximately 12% viable hybrids |
| Total wells positive by first ELISA | 30/148 | 6 were significantly higher than control in binding to ODC in the ELISA |
| Wells cloned by limiting dilution | 30 | All positive polyclones expanded and cloned |
| Total individual ELISA-positive monoclones recovered from 30 original polyclonal wells | 27 | Three polyclonal wells yielded no positive monoclones |
| Total monoclones secreting IgM/number tested | 27/27 | No comment |
| Total monoclones secreting IgG/number tested | 0/27 | |
| Total monoclones precitating ODC activity/number tested | 1/5 | Only one precipitated a significant amount of ODC activity over control media |

Table IV shows that of the twenty-seven monoclonal cell lines were developed, 100 % of which secreted antibody of the IgM subclass. Again these antibodies were later found to be inadequate for utilization as ODC-specific reagents.

EXAMPLE 8

FACS (Flow Activated Cell Sorting) Procedure

IgM secreting hybridoma cells 238–57 ADR were centrifuged at 500×g for 3 minutes, washed three times with PBS and resuspended in 3ml of PBS. Fluorescein conjugated affinity purified $F(ab)_2$ fragment goat anti-mouse immunoglobulin IgM (Cappel) was diluted 1:100 in PBS (1×) and 20–40 $\mu l$ was added to 20 $\mu l$ cell suspension. After incubation for 15–20 minutes in the dark at room temperature, the cells are washed twice with PBS centrifuging at 500 ×g for 3 minutes. An aliquot of 300 $\mu l$ of paraformaldehyde (1% in PBS) was added to fix the cells. The cells were incubated at 4° C. until sorted by flow cytometry. For indirect staining hybridoma cells were first incubated with rat anti-mouse IgM antibody 2G10, washed, then stained with the fluorescein $F(ab)_2$ fragment goat anti-mouse immunoglobulin IgM and sorted by flow cytometry.

EXAMPLE 9

Magnetic Cell Separation

Mouse hybridoma cells 238-57 ADR were washed three times in Iscove's medium containing 1% fetal bovine serum and 0.1% gentamicin. The cells were centrifuged at 500 ×g for three minutes at room temperature and then counted. The pellet was resuspended in 0.5 ml medium and incubated for 60 minutes on ice with purified rat anti-mouse IgM antibody (2G10) at a concentration of approximately 0.425 mg/ml (about 0.1 ml was used per 10⁶ cells/ml). After washing twice in cold Iscove's medium, the cells were resuspended in 0.2 ml medium and counted. Magnetic beads were washed 3 times in serum-free medium using a magnetic board. The cell pellet was mixed with the bead pellet at a ratio of 20 beads/cell. The total volume should not exceed 0.4 ml. The cell/bead mixture was incubated for ½ hour on ice, agitating every 10 minutes.

The cell/bead mixture was resuspended in at least 2 ml of medium and separated magnetically perpendicular to gravity.

Once separation was complete, the supernatant was removed without disturbing the magnetic pellet. The beads were resuspended in 1–2 ml medium and observed microscopically.

EXAMPLE 10
Lymphocyte Study With 2G10 Gelonin Conjugate

To demonstrate the cytotoxicity of the 2G10 gelonin conjugate, two Balb/c female mice (Harlan Sprague Dawley) were sacrificed and spleens were excised. In a laminar flow hood, the skin was washed above the spleen with 70% isopropyl alcohol and cut open with aseptic or autoclaved scissors. Using a pair of sterile forceps and scissors, the peritoneum was cut open exposing the spleen. The spleen was placed in a 100 mm sterile petri dish containing 10–15 ml growth media (Iscoves;Gibco) with 10% fetal bovine serum (Hyclone) and 50 $\mu$g/ml gentamicin (Tri-Bio Laboratories). The spleen was swirled in the media and then transferred to a clean petri dish with fresh growth media and covered.

Preparation of Lymphocytes

In a laminar flow hood and using sterilized instruments, the excess fat and connective tissue (white material) was cut from the spleens. The spleens were tranferred to a new petri dish with about 20 ml growth media with forceps. The wash procedure was repeated twice. The spleens were dispersed using two 10 ml syringes with 18 gauge needles until there were no longer any large sections of spleen remaining. Spleen cells (splenocytes) appeared as cloudy mixtures in growth media and contained both red and white cells. The cells and media were pipetted into a 50 ml centrifuge tube (Corning) and any large non-dispersed sections of tissue was excluded. Growth media was added to the bottom of the petri dish and removed after swirling in 10 ml growth media. The cells were placed on ice in the closed tube for 10 minutes.

The top portion was pipetted off (leaving behind the larger sections of non-dispersed tissues). After centrifugation for 10 minutes at 1800 revolutions per minute (rpm) in a DuPont Sorvall 2LC-2B table top centrifuge, the supernatant was discarded. The pellet was re-suspended in 10 ml of growth media and the cells were counted using 5 ul of cell suspension and 95 ul of a 1:2 dilution of trypan blue solution using a hemocytometer and a Nikon phase contrast microscope at 100×magnification. The total cell count was $6.24 \times 10^8$ cells. The solution was brought up to 20 ml resulting in $3.12 \times 10^7$ cells/ml growth media. One ml of this cell suspension was added to each of 15 ml centrifuge tubes.

The groups consisted of group 1: Control-media only added to cells; group 2: Control-media only added to cells; group 3: Control-media only added to cells; group 4: 2G10 Antibody (Ab) at 1 $\mu$g/ml; group 5: 2G10 Antibody at 0.1 $\mu$g/ml; group 6: 2G10 Antibody at 0.01 $\mu$g/ml; group 7: gelonin at 1 $\mu$g/ml equivalent =0.2 $\mu$g/ml; group 8: gelonin at 0.1 $\mu$g/ml equivalent=0.02 $\mu$g/ml; group 9: gelonin at 0.01 $\mu$g/ml equivalent=0.002 $\mu$g/ml; group 10: Ab+Gelonin at 0.5 $\mu$g/ml Ab+0.1 $\mu$g/ml gelonin; group 11: Ab+Gelonin at 0.05 $\mu$g/ml Ab+0.02 $\mu$g/ml gelonin; group 12: Ab+Gelonin at 0.005 $\mu$g/ml Ab+0.002 $\mu$g/ml gelonin; group 13: 2G10+ Gelonin conjugate at 1 $\mu$g/ml; group 14: 2G10+Gelonin conjugate at 0.1 $\mu$g/ml; and group 15: 2G10+Gelonin conjugate at 0.01 $\mu$g/ml.

The protein was added to the respectively numbered tubes and the total volume of each was brought to 5 ml with Iscoves growth media. The caps of the tubes were loosened and the tubes were incubated for 24 hours in a 37° C. $CO_2$ incubator (Queue) (5% $CO_2$–95% air). The tubes were then centrifuged at 1500 rpm for 10 minutes in an IEC Centra-7R centrifuge at 4° C. The supernatant was removed and saved. The cell pellets were resuspended in 10 ml growth media and centrifuged. The supernatant was discarded and cells washed twice with 4–5 ml growth media by centrifugation.

The treated cells were transferred in 5 ml growth media to a 6-well plate (Falcon) and incubated at 37° C. in a $CO_2$ incubator. On specified days thereafter, 300 $\mu$l of growth media was collected into a numbered microcentrifuge tube. 1 $\mu$l of 10% sodium azide was added to each tube and stored at 4° C. Growth media samples were taken after 24 hours, 72 hours, 96 hours. An Enzyme-linked immunosorbant assay was used to determine the effect of treatment on IgM secretion from primary lymphocyte culture.

50 $\mu$l of a 2 mg/ml concentration of goat anti-mouse IgG (whole antibody) (Sigma) was dissolved in 12 ml of double distilled water ($ddH_20$). Using a multi-channel pipetter (Titer-Tek), 50 $\mu$l of this solution was placed in each well of 96-well microtiter plate (Falcon) resulting in each well receiving 500 ng of goat-produced antibody against mouse immunoglobulin G and dried overnight by incubating uncovered in a 37° C oven. 100 $\mu$l of 5% BSA in 1× phosphate buffered saline (PBS) was added to each well of the 96-well plate and incubated 1.5 hours at room temperature. The liquid was removed by inverting the plate on paper towels. Each well of the 96-well plate was rinsed with PBS 1× containing Tween-20 (0.05%) (Biorad) and the liquid was removed by inverting the plate and tapping dry on paper towels. 100 $\mu$l of each supernatant was added to individual wells of the 96-well plate and incubated 1.5 hours at room temperature. The wells were rinsed thrice with PBS Tween-20 and 100 $\mu$l of goat produced antibody against mouse immunoglobulin mu chain chemically conjugated to horseradish peroxidase enzyme (Sigma) diluted 1:1000 in 1 mg/ml BSA in PBS was added and incubated 1.5 hours at room temperature. 100 $\mu$l ABTS ((2, $2^1$-azino-bis (3-ethyl benz thiazoline -6-sulfonic acid)) (Sigma)) in 0.1 in sodium citrate buffer (pH 4.2) with 0.03% hydrogen peroxide (11 $\mu$l of 30% $H_20_2$ in 11 mls ABTS) was added and after 20 minutes at room temperature, the plate was placed the plate in a Bio-Tek Laboratories Microplate Autoreader and absorbance values were read. The conjugate of the present invention significantly inhibited IgM secretion from primary lymphocytes at 24 hours (FIG. 11), 48 hours (FIG. 12) and 72 hours (FIG. 13). The results shown in FIGS. 11–13 illustrate that the conjugate treatment dose-dependently reduced the level of IgM in these primary lymphocyte cultures. The other treatments were unable to alter IgM levels at any of the dose levels tested. Therefore, through covalent association of 2G10 anti-mouse IgM monoclonal antibody with gelonin, the level of IgM produced by lymphocytes was suppressed.

EXAMPLE 11

Lymphocyte Study #2 With 2G10-Gelonin Conjugate

The procedure was the same as in Example 10 except that the final protein concentrations were 5 $\mu$g, 0.5 $\mu$g and 0.05 $\mu$g or equivalent molar concentration for gelonin.

FIGS. 14–16 show that the conjugate of the present invention strongly inhibited the secretion of IgM from primary lymphocytes at 24, 48 and 72 hours, respectively.

EXAMPLE 12

Lymphocyte Study #3 With 2G10-Gelonin Conjugate

The cells were prepared as in Examples 10 and 11 except that they were exposed to treatment (by control, antibody, gelonin, Ab+gelonin and conjugate) for 2 hours on ice. The cells were then centrifuged and washed twice with media and transferred to six well plates and incubated. Supernatant samples were collected at 24, 48, 72 and 96 hour intervals. The protein final concentration was 5 $\mu$g/ml (or equivalent for gelonin). A new 2G10-gelonin conjugate was made and tested along with the former conjugate.

FIGS. 17–20 show that the conjugates of the present invention clearly inhibited the secretion of IgM antibody from lymphocytes at 24, 48, 72 and 96 hours, respectively. Clearly, the short term incubation with immunoconjugate was sufficient to mediate changes in IgM secretion from plasma cells.

EXAMPLE 13
Fusion of Murine (Balb/C) Spleen Cells With Murine Myeloma Cells (P3×AG63×8)

The growing media for P3×AG63×8 myeloma cells was Iscoves (Gibco) with 500 ml containing 10% fetal bovine serum (Hyclone) and 0.5% ml gentamicin (Tri-Bio Laboratories). An 8-azo-guanine (20 µg/ml) solution was substituted for regular growing media for the (P3×AG63×8) myeloma about 1 week before time of fusion. The HAT solution consisted of 0.5 ml gentamicin, 5 ml 100×HT, 5 ml 100×A and 20% FBS (fetal bovine serum). The 100×HT solution consisted of 136 mg hypoxanthine (10 mM) and 39 mg thymidine (1.6 mm) in 100 ml ddH$_2$0 (warmed to 70–80° C.). The 100×A consisted of 1.8 mg aminopterin/100 ml H$_2$0, pH 7.8.

Fusion was performed with the spleen cells washed 4× in serum-free gentamicin-free media by centrifugation for 5 minutes at 200 ×g (1000 rpm in Sorvall table-top GLC-2B centrifuge). After resuspension in 10 ml serum-free media, the cells were diluted 1:20 (5 µl in 100 µl media) and counted in a hemocytometer.

Flasks about 50–60% confluent with P$_3$ myeloma cells were used and cells were collected by centrifugation and washed 4 times in serum-free media (5 minutes at 500 µg) and the cells were counted. The spleen and P$_3$ cells were combined in 4:1 ratio (8×10$^7$ spleen cells and 2×10$^7$ myeloma cells) and pelleted together by centrifugation for 5 minutes at 1200 rpm. One ml of cold PEG-4000-DMSO solution was added and cells incubated in this mixture for 15 seconds, then diluted in PEG-DMSO slowly with 20 mls serum-free media added drop-wise over a 3 minute period. The cell mixture was centrifuged at 400 ×g (166 rpm) for 6 minutes and the PEG diluent was completely aspirated. The cells were re-suspended in 50 ml 1×HAT and distributed with a multi-channel pipetter into five 96-well plates (Falcon) 100 µl/well and incubated. After cells were plated, they were left in an incubator for 3–4 days prior to addition of 100 µl fresh HAT media and left until, colonies formed.

EXAMPLE 14
IgM and IgG Screening

When the fusion cells supernatants yellowed, IgM and IgG secretions were screened using an ELISA assay. Briefly, 10 rigid 96-well microtiter plates (Falcon) were coated with 500 ng/well goat anti-mouse IgG (whole) (2 mg/ml) antibody by diluting 120 µl in 96 ml ddH$_2$0 and plated 50 µl/well using a multi-channel pipetter and dried overnight in a 37° C. oven uncovered. The solution was blocked with 5% bovine serum albumin in PBS by adding 100 µl to each well and incubating 1.5 hours at room temperature. After washing 3× with PBS containing 0.05% Tween-20 (Bio-Rad), 50 µl was pipetted into each well into two separate plates (one for IgG testing and one for IgM testing). Replacement growing media was added to fusion plate and incubated 1.5 hours at room temperature before washing 3× with PBS Tween-20. The secondary antibody examined for IgM presence was goat×mouse IgM—specific peroxidase (Sigma) diluted 1:1000 in 1 mg/ml BSA in 1×PBS. The secondary antibody examined for IgG presence was goat×mouse IgG—specific peroxidase (Sigma) diluted 1:1000 in 1 mg/ml BSA in 1×PBS. The secondary Ab was added to the respective plates and incubated 1.5 hours at room temperature and then washed 3 times with PBS Tween-20. Detection was made by the addition of 100 µl of ABTS (2, 2$^1$-azino-bis (3-ethyl benz thiazoline-6-sulfonic acid) containing 0.03% hydrogen peroxide and the plates were read on a Bio-Tek Instruments Microplate Autoreader at 405 nm.

Figure 21:
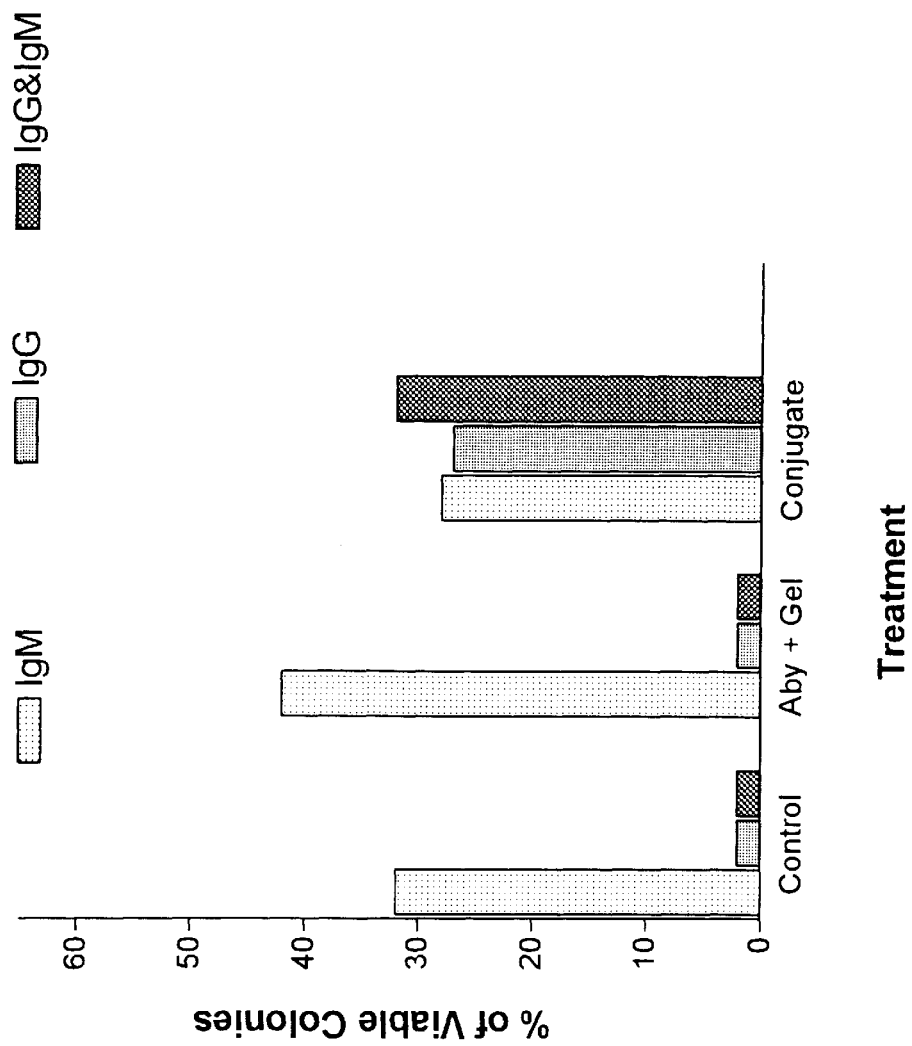
FIG. 21 shows the comparison of IgG and IgM secretion in conjugate and AB/gel (antibody/gelonin) treated fusions.

EXAMPLE 15
Fusion of (P3×AG63×8) Murine Myeloma Cells With Spleens of Treated Balb/c Female Mice The treatment groups were #1: control mouse-PBS; #2: 2G10 antibody and gelonin; and #3: conjugate. The conjugate was administered i.p. in a concentration of 500 µg/500 µl PBS on day 1 and day 4. The 2G10 antibody and gelonin mixture was administered to the mouse in the concentration of 250 µg antibody+50 µg gelonin in 500 µl PBS on day 1 and day 4. The control was administered i.p. in 500 µl on day 1 and day 4. On day 9, spleens were excised and cells prepared as described above. Then each spleen sample was fused with an equal number of myeloma cells using for each fusion 8×10$^7$ spleen cells+2'10$^7$ myeloma cells. The supernatants were screened one week later for IgG and IgM secreting antibodies in each group and assayed. The percentage of viable colonies secreting IgM and IgG, and those wells which contained both IgM and IgG secreting antibodies are shown in FIG. 21. FIG. 21 shows that IgM was the major form of immunoglobulin secreted from the viable cells derived from animals receiving saline or the mixture of 2G10 and gelonin. Immunoconjugate treatment significantly increased (from 3 to 30%) the number of colonies secreting IgG and colonies secreting IgG and IgM (as evidenced by specific detection of IgG and IgM in the spent culture supernatant wells containing colonies. Thus, the immunoconjugate enhances the number of viable colonies and IgG secretion by viable colonies following cell fusion. Virtually all colonies were secreting some form of immunoglobulin. These results show the in vivo effects of immunoconjugate on immunoglobulin expression in an intact animal following immortalization of their lymphocytes by cell fusion. Immunoconjugate treatment of animals would be useful in inducing IgG production in vitro following normal cell fusion immortalization protocols in monoclonal antibody production schemes.

EXAMPLE 16
IgM Detection in Serum of Pre-Treated KLH-Immunized Mice I

Balb/c female mice were treated and immunized according to the following schedule. On day 0, 150 µl of blood was collected from the end of the tail of each mouse into a 0.5 microcentrifuge tube, microcentrifuged for 10 minutes and the serum carefully pippeted into a clean, labeled centrifuge tube. These tubes were stored at −20° C. until assayed. After the blood was taken, the first treatment was given. The mice were divided into 4 groups—2 mice/group. The first group was of control mice and received 500 µl phosphate buffered saline i.p.; the second group received an i.p. injection of 500 µg 2G10 antibody in PBS (500 µl). The third group received 100 µg gelonin (a 500 µg molar equivalent dose) in 500 µl PBS and the fourth group received an i.p. injection of the 2G10-gelonin conjugate. A dose of 500 µg in 500 µl PBS was given i.p.

On day 2, a second treatment was given to each mouse to equal exactly ½ the amount of the first treatment. That is, 250 µg (or equivalent) in 250 µl PBS. Control mice received 250 µl PBS only. All injections were i.p. On day 4, the third treatment was the same as the second. On day 5, a blood sample was again taken from each mouse and the first KLH (keyhole-limpet-hemocyanin-DNP (dinitrophenol) (Calbiochem) immunization was given). A dose of 250 μg DNP-KLH in 200 μl PBS was injected into each mouse i.p. On day 6, the fourth treatment was given i.p.: Control—125 μl PBS; Antibody—125 μl in 125 μl PBS; gelonin-50 μl in 125 μl PBS; and Conjugate—125 μl in 125 μl PBS.

On day 8, the fifth treatment was given. The dose was the same as the fourth treatment. On day 10, blood samples were taken. The sixth treatment, which was the same as the fifth treatment, was given. On day 12, the seventh treatment was given. The dose was 250 μg/250 μl and control mice were given 250 μl PBS. On day 13, a KLH booster was given. The booster was the same as the first immunization. On day 20, blood samples were taken.

Figure 22:
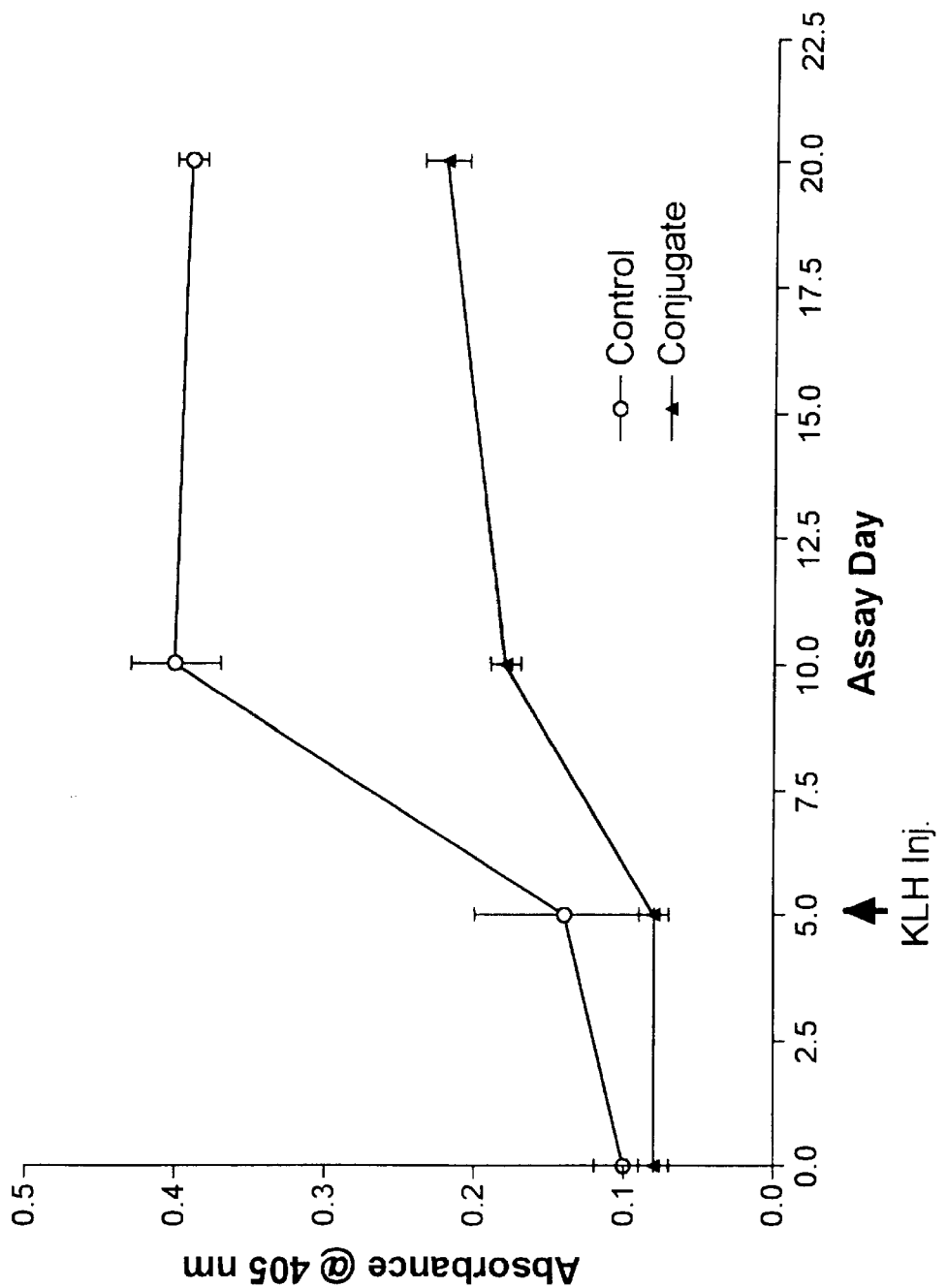
FIG. 22 shows the detection of IgM in serum of pretreated KLH-immunized mice I.

On day 20, serum samples were assayed. To assay for IgM in serum of pre-treated KLH-immunized mice: four 96-well plates were coated with 150 ng DNP-KLH per well in 50 μl. 57.6 μl of 2.5 mg/ml KLH-DNP were taken in 48 ml ddH$_2$0. Using a multi-channel pipetter, 50 μl was added to each well in four plates, left uncovered and dried overnight in 37° C. oven. Plates were blocked with 100 μl/well of 5% BSA in PBS and incubated 1.5 hours at room temperature. After washing 3x with PBS Tween-20, each serum sample was diluted 1:500 in 1 mg/ml BSA in PBS (2 μl/1 ml). 100 ul was put in each well and incubated 1.5 hours at room temperature. After washing 3x with PBS Tween-20, 100 ul of the secondary antibody—goatxmouse IgM peroxidase (Sigma) was added. The sample was diluted 1:2000 in 1 mg/ml BSA-PBS and incubated 1.5 hours at room temperature. After washing 3xwith PBS Tween-20, 100 μl ABTS with 0.03% H$_2$0$_2$ was added and read at 405 nm in Bio-Tek Microplate Autoreader. FIG. 22 shows that the conjugate of the present invention suppresses IgM response to KLH in vivo demonstrating effectiveness of immunoconjugate in animals.

EXAMPLE 17
IgM Detection in Serum of Pre-Treated KLH-Immunized Mice II

Figure 23:
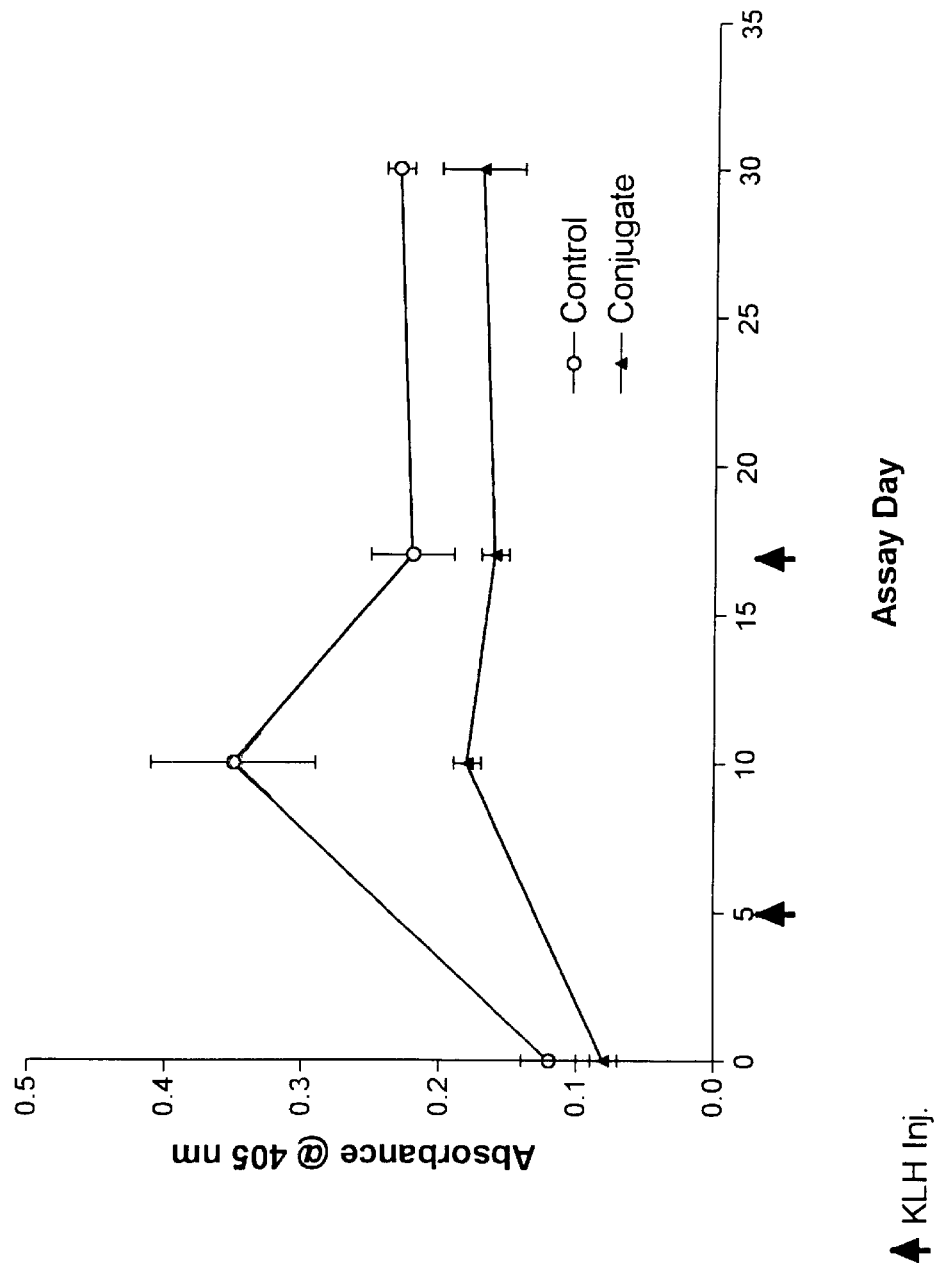
FIG. 23 shows the detection of IgM in serum of pretreated KLH-immunized mice II.

Balb/c female mice were treated and immunized according to the following schedule. On day 0, blood samples were collected from each mouse and stored. On day 1, the mice were divided into four groups: group 1 was of control mice given 500 μl phosphate buffered saline i.p. Group 2 received 100 μg (a 500 μl equivalent dose) of gelonin in 500 μl PBS i.p. injection. Group 3 received an antibody-gelonin mixture consisting of 250 μg 2G10 antibody+50 μg gelonin in 250 μl PBS i.p. injection. Group 4 received 500 μg of 2G10-Gelonin conjugate in 500 μl PBS by i.p. injection. On day 4, a second treatment was given. On day 5, a KLH immunization consisting of 250 μg KLH-DNP in 200 μl PBS. On days 12 and 18, blood was collected. On day 19, the third treatment was given (same as first and second treatments). On day 20, the KLH booster was given (same as first immunization). On day 29, blood was taken. On day 36, serum was assayed for IgM presence in the serum of the pre-treated KLH-immunized mice. FIG. 23 shows results similar to FIG.22.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An anti-IgM antibody conjugate comprising: a monoclonal antibody which binds selectively to IgM antibody, does not bind to IgG$_1$ or IgG$_2$ antibody, has a G isotype; and a cytotoxic moiety conjugated to said monoclonal antibody.

2. The conjugate of claim 1, wherein said monoclonal antibody binds to hybridoma cells producing an IgM antibody.

3. The conjugate of claim 1, wherein said monoclonal antibody is produced by ratxrat or ratxmouse hybridoma or progeny of said hybridoma.

4. The conjugate of claim 1, wherein said monoclonal antibody is labeled with a detectable label.

5. The conjugate of claim 1, wherein the cytotoxic moiety is gelonin.

6. A method of killing IgM antibody producing cells comprising contacting said cells with a cytocidally effective amount of the conjugate of claim 5.

7. An anti-IgM antibody conjugate comprising: a monoclonal antibody which binds selectively to murine IgM antibody, doe not bind to IgG$_1$ or IgG$_2$ antibody, and has a G isotype; and a cytotoxic moiety conjugated to said monoclonal antibody.

8. The conjugate of claim 7, wherein said monoclonal antibody binds to hybridoma cells producing an anti-mouse IgM antibody.

9. A The conjugate of claim 7, wherein said monoclonal antibody is labeled with a detectable label.

10. The conjugate of claim 2, wherein said monoclonal antibody is produced by a ratxrat or ratxmouse hybridomas or progeny of said hybridomas.

11. The conjugate of claim 2, wherein the cytotoxic moiety is gelonin.

12. A method of killing murine IgM antibody producing cells comprising contacting said cells with a cytocidally effective amount of the conjugate of claim 7.

* * * * *